US009655737B2

(12) United States Patent
Perloff et al.

(10) Patent No.: US 9,655,737 B2
(45) Date of Patent: May 23, 2017

(54) EXPANDABLE INTERBODY SPACER

(71) Applicant: GLOBUS MEDICAL, INC., Audubon, PA (US)

(72) Inventors: Jonathan Perloff, Slatington, PA (US); Christopher Saville, Morgantown, PA (US); Robert H. Wriggins, Jr., Tuckahoe, NJ (US); Jason Pastor, Philadelphia, PA (US); William Rhoda, Media, PA (US); Mark Fromhold, Ardmore, PA (US)

(73) Assignee: Globus Medical, Inc., Audubon, PA (US)

( * ) Notice: Subject to any disclaimer, the term of this patent is extended or adjusted under 35 U.S.C. 154(b) by 82 days.

(21) Appl. No.: 14/743,493

(22) Filed: Jun. 18, 2015

(65) Prior Publication Data
US 2015/0313719 A1    Nov. 5, 2015

Related U.S. Application Data

(63) Continuation of application No. 13/837,209, filed on Mar. 15, 2013, now Pat. No. 9,278,008, which is a
(Continued)

(51) Int. Cl.
A61F 2/44       (2006.01)
A61F 2/46       (2006.01)
A61F 2/30       (2006.01)

(52) U.S. Cl.
CPC ............ *A61F 2/442* (2013.01); *A61F 2/4425* (2013.01); *A61F 2/4455* (2013.01);
(Continued)

(58) Field of Classification Search
CPC .......... A61F 2/44; A61F 2/442; A61F 2/4425; A61F 2/46; A61F 2/4611; A61F 2002/4415
(Continued)

(56) References Cited

U.S. PATENT DOCUMENTS 5,171,278 A    12/1992  Pisharodi
5,545,229 A     8/1996  Parsons
(Continued)

FOREIGN PATENT DOCUMENTS

WO    2010105181 A1    9/2010
WO    2012047712 A1    4/2012

*Primary Examiner* — Ellen C Hammond
*Assistant Examiner* — Christina Negrellirodrigue

(57) ABSTRACT

Embodiments of the present disclosure relate to devices and methods for treating one or more damaged, diseased, or traumatized portions of the spine, including intervertebral discs, to reduce or eliminate associated back pain. In one or more embodiments, the present disclosure relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable interbody spacer. The first jointed arm and the second jointed arm may be interconnected at a distal end of the expandable interbody spacer.

18 Claims, 35 Drawing Sheets

Related U.S. Application Data continuation-in-part of application No. 13/483,852, filed on May 30, 2012, now Pat. No. 9,044,342.

(52) U.S. Cl.
CPC ..... *A61F 2/4611* (2013.01); *A61F 2002/3093* (2013.01); *A61F 2002/30148* (2013.01); *A61F 2002/30149* (2013.01); *A61F 2002/30387* (2013.01); *A61F 2002/30405* (2013.01); *A61F 2002/30471* (2013.01); *A61F 2002/30476* (2013.01); *A61F 2002/30482* (2013.01); *A61F 2002/30525* (2013.01); *A61F 2002/30545* (2013.01); *A61F 2002/30579* (2013.01); *A61F 2002/30772* (2013.01); *A61F 2002/30827* (2013.01); *A61F 2002/30836* (2013.01); *A61F 2002/30904* (2013.01); *A61F 2002/4623* (2013.01); *A61F 2002/4627* (2013.01); *A61F 2230/0073* (2013.01); *A61F 2310/00017* (2013.01); *A61F 2310/00023* (2013.01); *A61F 2310/00179* (2013.01)

(58) Field of Classification Search
USPC ......... 606/246–249, 279, 96, 99, 104, 86 A; 623/17.11–17.16
See application file for complete search history.

(56) References Cited

U.S. PATENT DOCUMENTS

| | | | |
|---|---|---|---|
| 5,665,122 A | 9/1997 | Kambin | |
| 5,693,100 A | 12/1997 | Pisharodi | |
| 5,865,848 A | 2/1999 | Baker | |
| 6,039,761 A | 3/2000 | Li | |
| 6,193,757 B1 | 2/2001 | Foley | |
| 6,409,766 B1 | 6/2002 | Brett | |
| 6,443,989 B1 | 9/2002 | Jackson | |
| 6,454,807 B1 | 9/2002 | Jackson | |
| 6,464,727 B1 | 10/2002 | Sharkey | |
| 6,478,823 B1 | 11/2002 | Michelson | |
| 6,572,653 B1 | 6/2003 | Simonson | |
| 6,685,742 B1 | 2/2004 | Jackson | |
| 6,695,882 B2 | 2/2004 | Bianchi | |
| 6,719,794 B2 | 4/2004 | Gerber | |
| 6,719,795 B1 | 4/2004 | Cornwall | |
| 6,723,126 B1 | 4/2004 | Berry | |
| 6,743,257 B2 | 6/2004 | Castro | |
| 6,821,298 B1 | 11/2004 | Jackson | |
| 6,833,006 B2 | 12/2004 | Foley | |
| 6,835,206 B2 | 12/2004 | Jackson | |
| 6,887,273 B2 | 5/2005 | Ralph | |
| 6,893,464 B2 | 5/2005 | Kiester | |
| 6,953,477 B2 | 10/2005 | Berry | |
| 6,974,480 B2 | 12/2005 | Messerli | |
| 7,018,413 B2 | 3/2006 | Kruger | |
| 7,052,515 B2 | 5/2006 | Simonson | |
| 7,074,239 B1 | 7/2006 | Cornwall | |
| 7,087,055 B2 | 8/2006 | Lim | |
| 7,094,257 B2 | 8/2006 | Mujwid | |
| 7,223,291 B2 | 5/2007 | Errico | |
| 7,223,292 B2 | 5/2007 | Messerli | |
| 7,261,739 B2 | 8/2007 | Ralph | |
| 7,270,680 B2 | 9/2007 | Ralph | |
| 7,273,498 B2 | 9/2007 | Bianchi | |
| 7,513,900 B2 | 4/2009 | Carrison | |
| 7,655,042 B2 | 2/2010 | Foley | |
| 7,763,074 B2 | 7/2010 | Altarac | |
| 2003/0236520 A1 | 12/2003 | Lim | |
| 2004/0102774 A1 | 5/2004 | Trieu | |
| 2004/0102847 A1 | 5/2004 | Sato | |
| 2005/0070911 A1 | 3/2005 | Carrison | |
| 2006/0089642 A1 | 4/2006 | Diaz | |
| 2006/0142858 A1* | 6/2006 | Colleran | A61F 2/4465 623/17.11 |
| 2006/0224241 A1 | 10/2006 | Butler | |
| 2006/0241643 A1 | 10/2006 | Lim | |
| 2007/0093899 A1 | 4/2007 | Dutoit | |
| 2008/0243255 A1* | 10/2008 | Butler | A61F 2/4465 623/17.16 |
| 2010/0174373 A1 | 7/2010 | Galley | |
| 2010/0222816 A1 | 9/2010 | Gabelberger | |
| 2011/0282459 A1 | 11/2011 | McClellan, III | |
| 2011/0295370 A1 | 12/2011 | Suh | |
| 2012/0004732 A1 | 1/2012 | Goel | |
| 2012/0123546 A1 | 5/2012 | Medina | |
| 2012/0209386 A1* | 8/2012 | Triplett | A61F 2/4465 623/17.16 |
| 2012/0245639 A1 | 9/2012 | Dwyer | |
| 2012/0245696 A1 | 9/2012 | Thibodeau | |
| 2012/0296379 A1 | 11/2012 | Morancy-Meister | |
| 2012/0296430 A1 | 11/2012 | Edie | |
| 2012/0296431 A1 | 11/2012 | Kim | |
| 2012/0310287 A1 | 12/2012 | Bao | |
| 2013/0079883 A1 | 3/2013 | Butler | |

\* cited by examiner

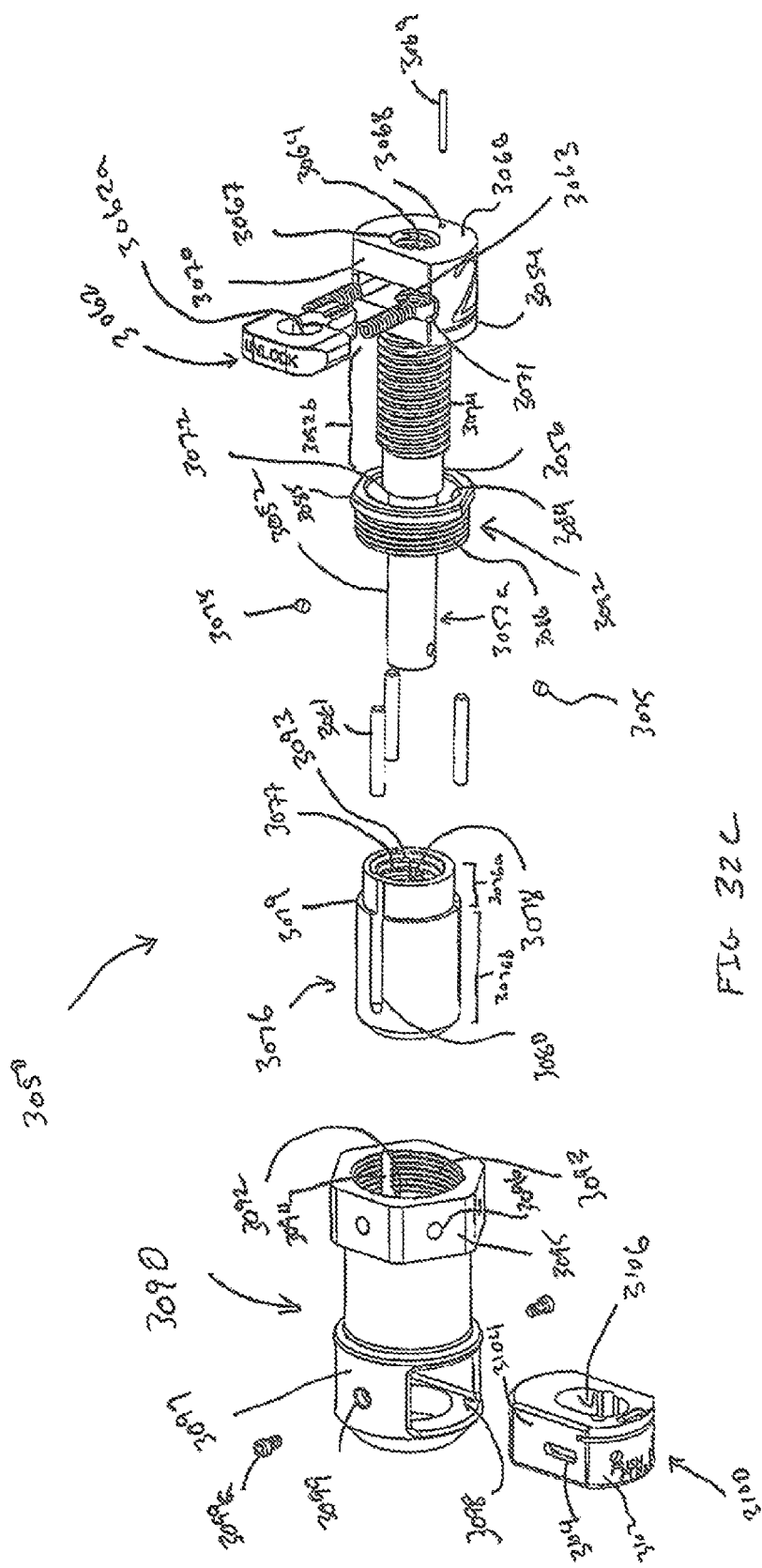

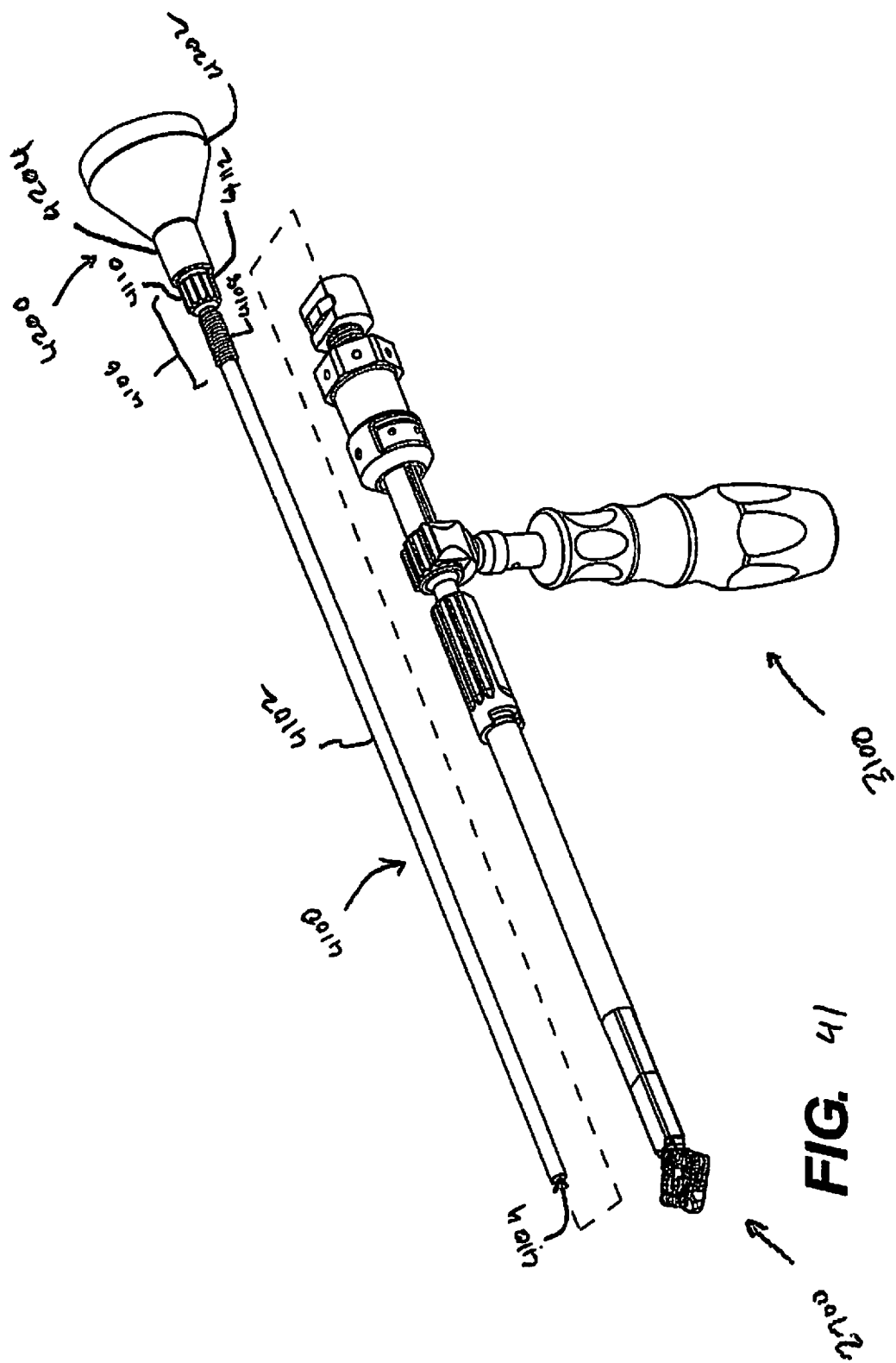

EXPANDABLE INTERBODY SPACER

CROSS-REFERENCE TO RELATED APPLICATIONS

This application is a continuation application of U.S. patent application Ser. No. 13/837,209, filed Mar. 15, 2013, which is a continuation-in-part of U.S. patent application Ser. No. 13/483,852, filed May 20, 2012, now issued as U.S. Pat. No. 9,044,342, which are hereby incorporated by reference in their entirety.

FIELD OF THE INVENTION

The present disclosure relates to embodiments of devices and methods for treating one or more damaged, diseased, or traumatized portions of the spine, including intervertebral discs, to reduce or eliminate associated back pain. In one or more embodiments, the present disclosure relates to an expandable interbody spacer. In addition, the present disclosure describes tools and methods for implanting the disclosed devices.

BACKGROUND OF THE INVENTION

The vertebrate spine is the axis of the skeleton providing structural support for the other body parts. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc.

The spinal disc and/or vertebral bodies may be displaced or damaged due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant, which may be referred to as an interbody spacer, can be inserted into the cavity created where the intervertebral disc was removed to help maintain height of the spine and/or restore stability to the spine. An example of an interbody spacer that has been commonly used is a cage, which typically is packed with bone and/or bone-growth-inducing materials. However, there are drawbacks associated with conventional interbody spacers, such as cages and other designs. For instances, conventional interbody spacers may be too large and bulky for introduction into the disc space in a minimally invasive manner, such as may be utilized in a posterior approach. Further, these conventional interbody spacers may have inadequate surface area contact with the adjacent endplates if sized for introduction into the disc space in a minimally invasive manner. In addition, conventional interbody spacers designed for introduction into the disc space in a minimally invasive manner may lack sufficient space for packing of bone-growth-inducing material, thus potentially not promoting the desired graft between the adjacent endplates.

Therefore, a need exists for an interbody spacer that can be introduced in a minimally manner that provides a desired amount of surface area contact with the adjacent endplates and has an increased space for packing of bone-growth-inducing material.

SUMMARY OF THE INVENTION

Embodiments of the present disclosure relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable interbody spacer. The first jointed arm and the second jointed arm may be interconnected at a distal end of the expandable interbody spacer. The first jointed arm and the second jointed arm may each be configured to fold inward in opposite directions to place the expandable interbody spacer in an expanded position.

BRIEF DESCRIPTION OF THE DRAWINGS

Embodiments of the present disclosure will be more readily understood with reference to the embodiments thereof illustrated in the attached drawing figures, in which:

FIG. 32C depicts an exploded view of the actuator assembly;

FIGS. 33-43 depict various views of components of the exemplary tool of FIG. 30 and their interaction with an exemplary interbody spacer.

Throughout the drawing figures, it should be understood that like numerals refer to like features and structures.

DETAILED DESCRIPTION OF THE INVENTION

Figure 1:
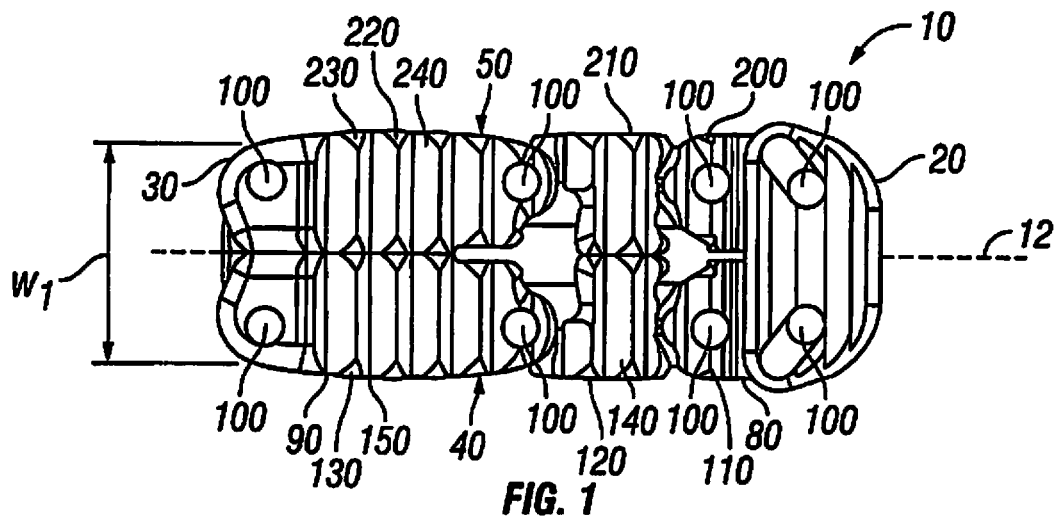
FIG. 1 is a top view of an expandable interbody spacer shown in a collapsed position in accordance with embodiments of the present disclosure.
Figure 2:
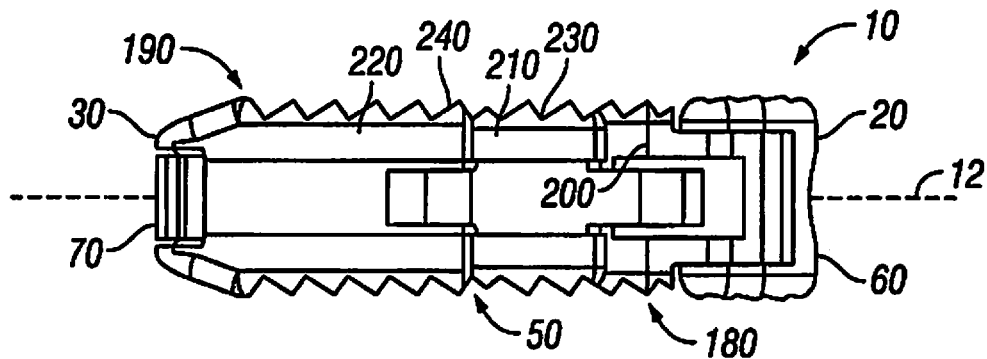
FIG. 2 is a side view of the expandable interbody spacer of FIG. 1 shown in a collapsed position.

The preferred embodiments of the disclosure will now be described with reference to the attached drawing figures. The following detailed description of the invention is not intended to be illustrative of all embodiments. In describing preferred embodiments of the present disclosure, specific terminology is employed for the sake of clarity. However, the embodiments described herein are not intended to be limited to the specific terminology so selected. It is to be understood that each specific element includes all technical equivalents that operate in a similar manner to accomplish a similar purpose.

As used herein, the term "proximal" may refer to a portion of a device or component thereof disposed closest to an operator or healthcare professional during an implantation procedure. Conversely, the term "distal" may refer to a portion of a device or component thereof disposed opposite the proximal portion and disposed farther from the operator or healthcare professional during an implantation procedure. As discussed below, the embodiments of expandable interbody spacers described herein may be implanted via any suitable approach known in the art. It is contemplated, however, that the disclosed embodiments may be implanted via an offset (e.g., 20-40 degree offset) posterior approach. Accordingly, solely for orientation purposes, a "proximal" portion of the device, when implanted, may be disposed posteriorly relative to a patient, if implanted via a posterior approach.

Referring to FIGS. 1-10, an expandable interbody spacer 10 is shown in accordance with embodiments of the present disclosure. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 15 of the spacer 10. The first and second jointed arms 40, 50 may be interconnected at the proximal end 20, for example, by a proximal connection member 60. The first and second jointed arms 40, 50 may be interconnected at the distal end 30, for example, by a distal connection member 70. The first and second jointed arms 40, 50 of the expandable interbody spacer 10 may be made from a number of materials, including titanium, stainless steel, titanium alloys, non-titanium alloys, polymeric materials, plastic composites, polyether ether ketone ("PEEK") plastic material, ceramic, elastic materials, and combinations thereof. While the expandable interbody spacer 10 may be used with a posterior, anterior, lateral, or combined approach to the surgical site, the spacer 10 may be particularly suited with a posterior approach.

The first jointed arm 40 has a proximal end 80 and a distal end 90. The proximal end 80 may be pivotally coupled to the proximal connection member 60. The distal end 90 may be pivotally coupled to the distal connection member 70. Any of a variety of different fasteners may be used to pivotally couple the proximal end 80 and the distal end 90 and the proximal connection member 60 and the distal connection member 70, such as pins 100, for example. In another embodiment (not illustrated), the connection may be a hinged connection. As illustrated, the first jointed arm 40 may comprise a plurality of links that are pivotally coupled to one another. In the illustrated embodiment, the first jointed arm 40 comprises first link 110, second link 120, and third link 130. When the spacer 10 is in a collapsed position, the first link 110, second link 120, and third link may be generally axially aligned. As illustrated, the first link 110, second link 120, and third link 130 may be connected end to end. When the spacer 10 is in a collapsed position, the first link 110, second link 120, and third link 130 may be generally axially aligned. The first link 110 and the second link 120 may be pivotally coupled, and the second link 120 and the third link 130 may also be rotatably coupled. Any of a variety of different fasteners may be used to pivotally couple the links 110, 120, 130, such as pins 100, for example. In another embodiment (not illustrated), the coupling may be via a hinged connection.

As best seen in FIGS. 1, 5-7, 9, and 10, an upper surface 140 of the first jointed arm 40 may be defined by the links 110, 120, 130. The upper surface 140 should allow for engagement of the first jointed arm 40 with one of the adjacent vertebral bodies. In some embodiments, the upper surface 140 may include texturing 150 to aid in gripping the adjacent vertebral bodies. Although not limited to the following, the texturing 150 can include teeth, ridges, friction-increasing elements, keels, or gripping or purchasing projections.

Figure 7:
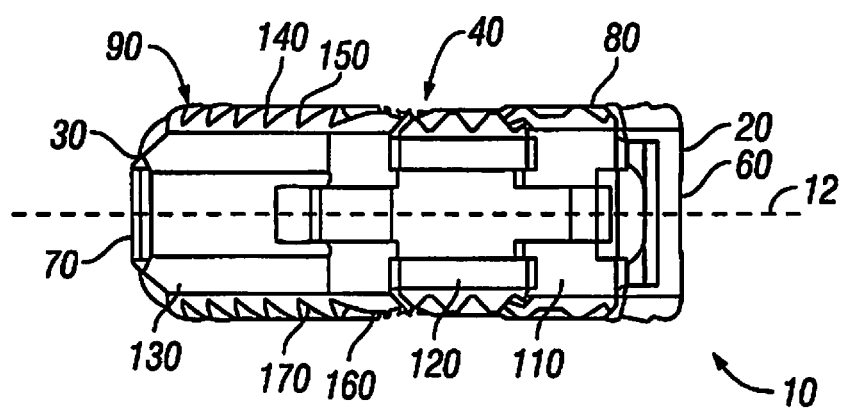
FIG. 7 is a right side view of the expandable interbody spacer of FIG. 1 shown in an expanded position.
Figure 9:
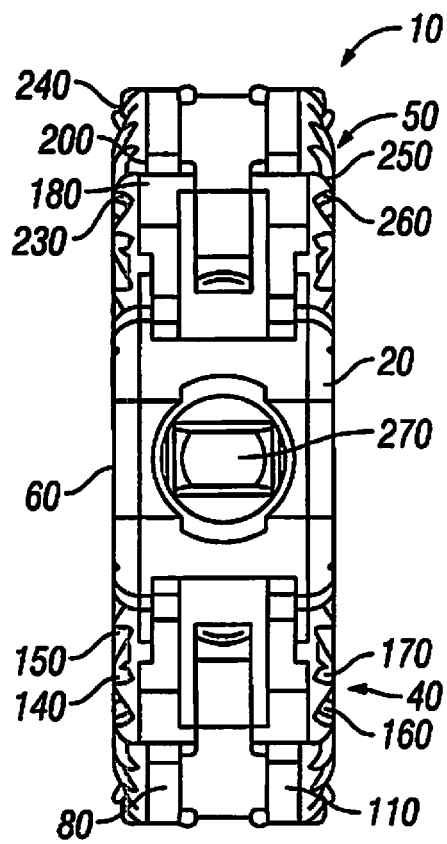
FIG. 9 is a proximal end view of the expandable interbody spacer of FIG. 1 shown in an expanded position.
Figure 10:
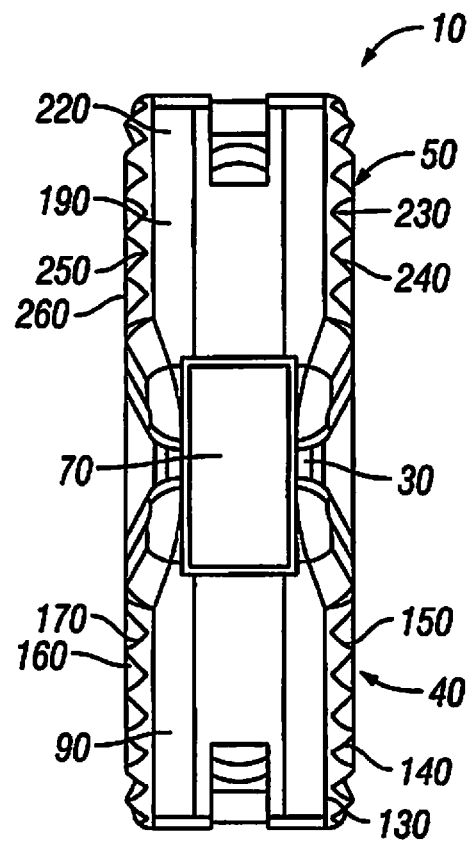
FIG. 10 is a distal end view of the expandable interbody spacer of FIG. 1 shown in an expanded position.

As best seen in FIGS. 7, 9, and 10 a lower surface 160 of the first jointed arm 40 may be defined by the links 110, 120, 130. The lower surface 160 should allow for engagement of the first jointed arm 40 with one of the adjacent vertebral bodies. In some embodiments, the lower surface 160 may include texturing 170 to aid in gripping the adjacent vertebral bodies. Although not limited to the following, the texturing 170 can include teeth, ridges, friction-increasing elements, keels, or gripping or purchasing projections.

The second jointed arm 50 has a proximal end 180 and a distal end 190. The proximal end 180 may be pivotally coupled to the distal connection member 70. The distal end 190 may be pivotally coupled to the distal connection member 70. Any of a variety of different fasteners may be used to pivotally couple the proximal end 180 and the distal end 190 and the proximal connection member 60 and the distal connection member 70, such as pins 100, for example. In another embodiment (not illustrated), the connection may be a hinged connection. As illustrated, the second jointed arm 50 may comprise a plurality of links that are pivotally coupled to one another. In the illustrated embodiment, the second jointed arm 50 comprises first link 200, second link 210, and third link 220. When the spacer 10 is in a collapsed position, the first link 200, second link 210, and third link 220 may be generally axially aligned. As illustrated, the first link 200, second link 210, and third link 220 may be connected end to end. The first link 200 and the second link 210 may be pivotally coupled, and the second link 210 and the third link 220 may also be pivotally coupled. Any of a variety of different fasteners may be used to pivotally couple the links 200, 210, 220, such as pins 100, for example. In another embodiment (not illustrated), the coupling may be via a hinged connection.

As best seen in FIGS. 1, 2, 6, and 8-10, an upper surface 230 of the second jointed arm 50 may be defined by the links 200, 210, 220. The upper surface 230 should allow for engagement of the second jointed arm 50 with one of the adjacent vertebral bodies. In some embodiments, the upper surface 230 may include texturing 240 to aid in gripping the adjacent vertebral bodies. Although not limited to the following, the texturing 240 can include teeth, ridges, friction-increasing elements, keels, or gripping or purchasing projections.

Figure 8:
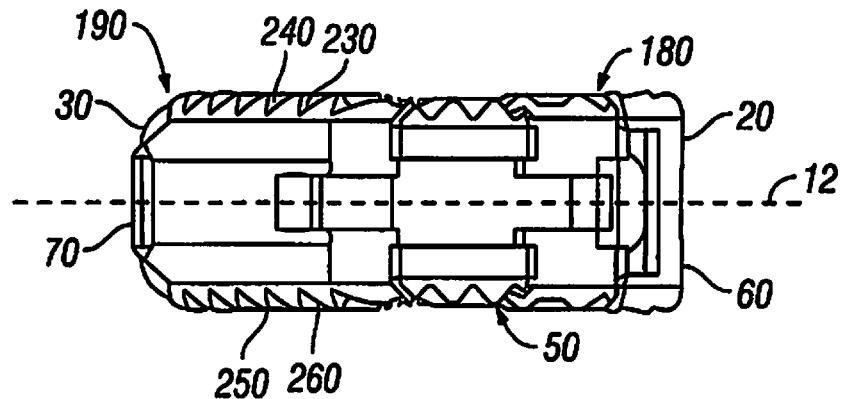
FIG. 8 is a left side view of the expandable interbody spacer of FIG. 1 shown in an expanded position.

As best seen in FIGS. 8-10, a lower surface 250 of the second jointed arm 50 may be defined by the links 200, 210, and 220. The lower surface 250 should allow for engagement of the second jointed arm 50 with one of the adjacent vertebral bodies. In some embodiments, the lower surface 250 may include texturing 260 to aid in gripping the adjacent vertebral bodies. Although not limited to the following, the texturing 260 can include teeth, ridges, friction-increasing elements, keels, or gripping or purchasing projections.

Figures 3, 4:
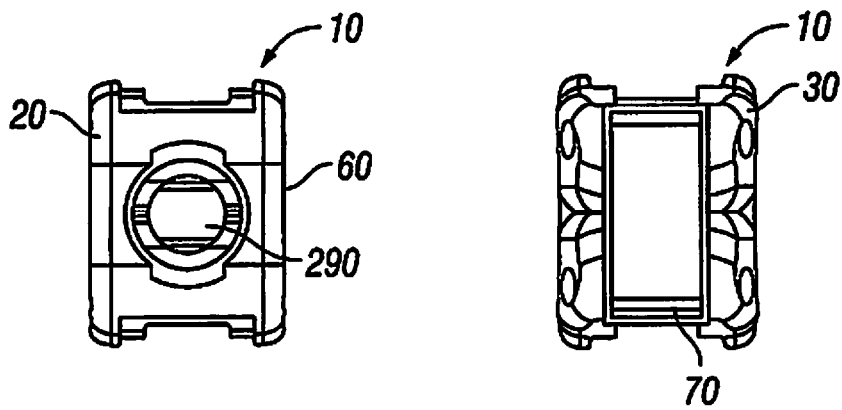
FIG. 3 is a proximal end view of the expandable interbody spacer of FIG. 1 shown in a collapsed position.
FIG. 4 is a distal end view of the expandable interbody spacer of FIG. 1 shown in a collapsed position.
Figure 5:
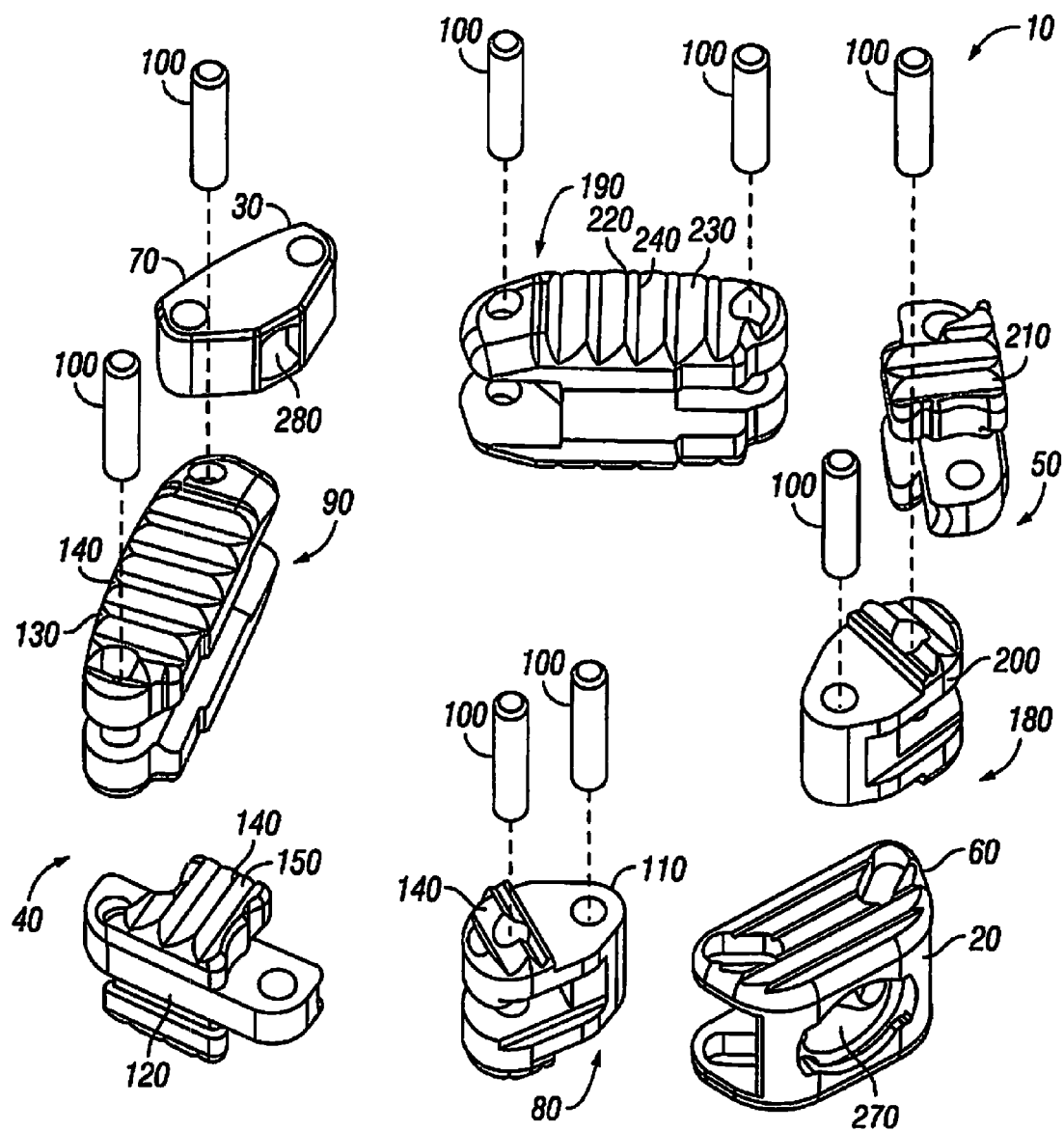
FIG. 5 is an exploded view of the expandable interbody spacer of FIG. 1.

With reference now to FIGS. 3, 5, and 9, a bore 270 extends through proximal connection end 60. The bore 270 may extend generally parallel to the longitudinal axis 12 (see FIG. 1) of the spacer 10. The first jointed arm 40 and the second jointed arm 50 may define a hollow interior portion (not shown) that extends axially through the spacer 10. The bore 270 in the proximal connection end 60 may communicate with this hollow interior portion. As best shown on FIG. 5, the distal connection end 70 may include an opening 280. As illustrated, the opening 280 may face inward and may not extend all the way through the distal connection 70. In one embodiment, the opening 280 may be generally aligned with the bore 270 in the proximal connection end 60 such at a tool (e.g., tool 340 shown on FIG. 12) inserted into the bore 270 may be received in the opening 280 for placement of the spacer 10 into a disc space and/or expansion of the spacer 10.

FIGS. 1-4 illustrate the expandable interbody spacer 10 in a collapsed position. In accordance with present embodiments, the expandable interbody spacer 10 may be laterally expanded to an expanded position. FIGS. 6-10 illustrate the expandable interbody spacer 10 in an expanded position. In the expanded position, the first arm 40 and the second arm 50 have each been folded inward in opposite directions. For example, the proximal end 80 and the distal end 90 of the first arm 40 may be folded closer together. The links 110, 120, 130 should pivot with respect to one another when the first arm 40 is folded inward. The proximal end 80 should pivot at the proximal connection end 60, and the distal end 90 should pivot at the distal connection end 70. By way of further example, the proximal end 180 and the distal end 190 of the second arm 50 may also be folded together. The links 200, 210, 220 should pivot with respect to another when the second arm is folded inward. The proximal end 180 should pivot at proximal connection end 60, and the distal end 190 should pivot at the distal connection end 70. After placement in the expanded position, the expandable interbody spacer 10 can be secured in the expanded position to prevent collapse of the expandable interbody spacer 10 upon application of spacer. Any of a variety of different techniques may be used to secure the expandable interbody spacer 10, including pins or other suitable locking mechanism, for example.

Figure 6:
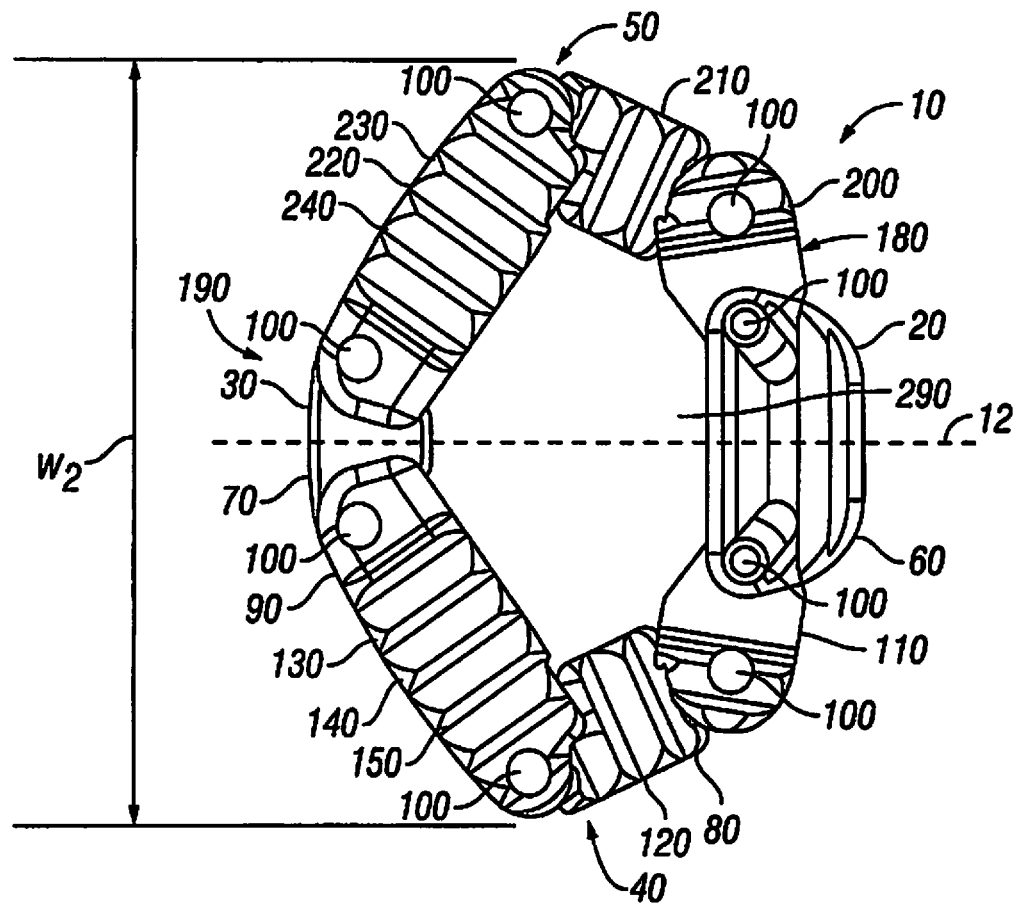
FIG. 6 is a top view of the expandable interbody spacer of FIG. 1 shown in an expanded position.

As illustrated by FIG. 6, the first and second jointed arms 40, 50 define an interior cavity 290 when in an expanded position. The interior cavity 290 may be filled with a bone-growth-inducing material, such as bone material, bone-growth factors, or bone morphogenic proteins. As will be appreciated by those of ordinary skill in the art, the bone-growth-inducing material should induce the growth of bone material, thus promoting fusion of the adjacent vertebra.

The expandable interbody spacer 10 may be sized to accommodate different applications, different procedures, implantation into different regions of the spine, or size of disc space. For example, the expandable interbody spacer 10 may have a width W1 (as shown on FIG. 1) prior to expansion of about 8 mm to about 22 mm and alternatively from about 10 mm to about 13 mm. By way of further example, the expandable interbody spacer 10 may be expanded to a width W2 (as shown on FIG. 6) in a range of about 26 mm to about 42 mm and alternatively from about 16 mm to about 32 mm. It should be understood that the width W1 or W2 whether prior to, or after, expansion generally refers to the width of the expandable interbody spacer 10 extending transverse to the longitudinal axis 12 of the spacer 10. In general, the width W2 of the expandable interbody spacer 10 after expansion should be greater than the width W1 of the expandable interbody spacer 10 prior to expansion.

Figure 11:
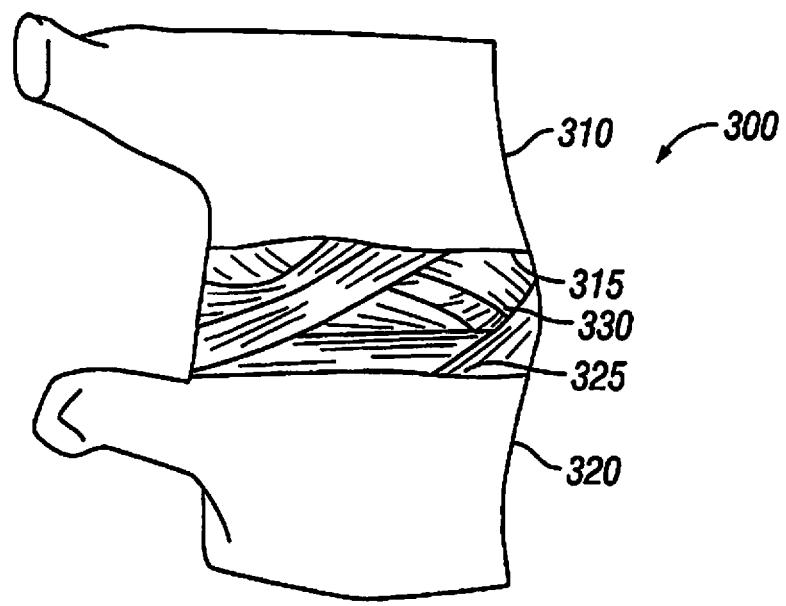
FIG. 11 is a view showing disc space between adjacent vertebrae in accordance with embodiments of the present disclosure.
Figure 12:
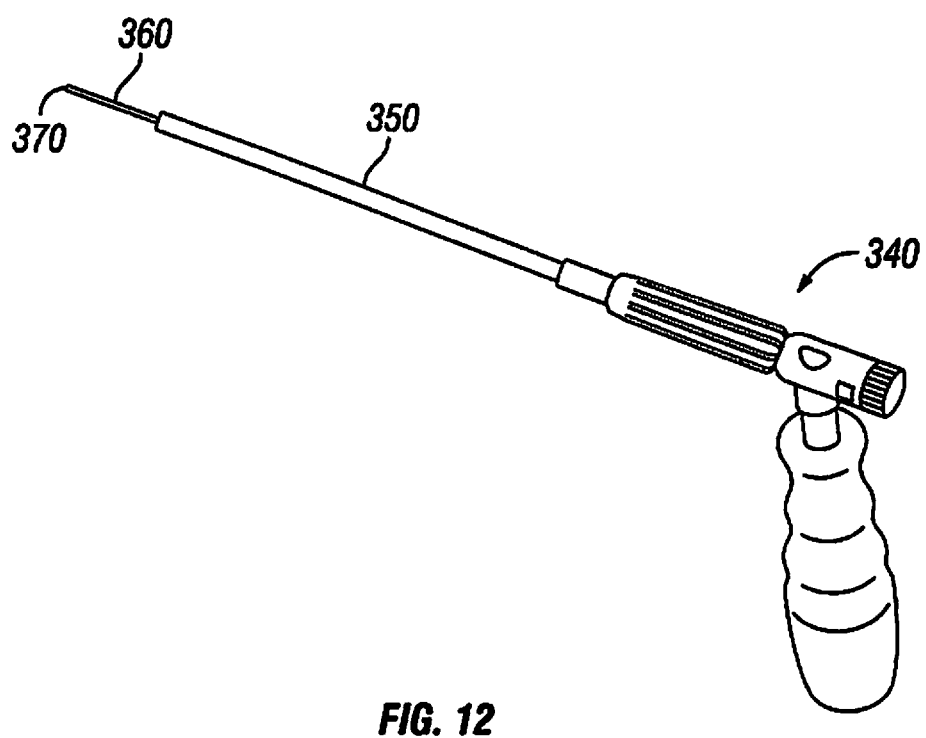
FIG. 12 is a view of a tool for insertion of an expandable interbody spacer in accordance with embodiments of the present disclosure.

In accordance with present embodiments, the expandable interbody spacer 10 may be used in the treatment of damage or disease of the vertebral column. In one embodiment, the expandable interbody spacer 10 may be inserted into a disc space between adjacent vertebrae in which the intervertebral disc has been partially or completely removed. FIG. 11 illustrates a spinal segment 300 into which the expandable interbody spacer 10 (e.g., FIGS. 1-10) may be inserted. The spinal segment 300 includes adjacent vertebrae, identified by reference numbers 310 and 320. Each of the adjacent vertebrae 310, 320 has a corresponding endplate 315, 325. The disc space 330 is the space between the adjacent vertebrae 310, 320. FIG. 12 illustrates a tool 340 that may be used in the insertion of the expandable interbody spacer 10 into the disc space 330. The tool 340 includes a shaft 350 having an elongated end portion 360 for coupling to the expandable interbody spacer 10. The elongated end portion 360 has a distal tip 370.

Figure 13:
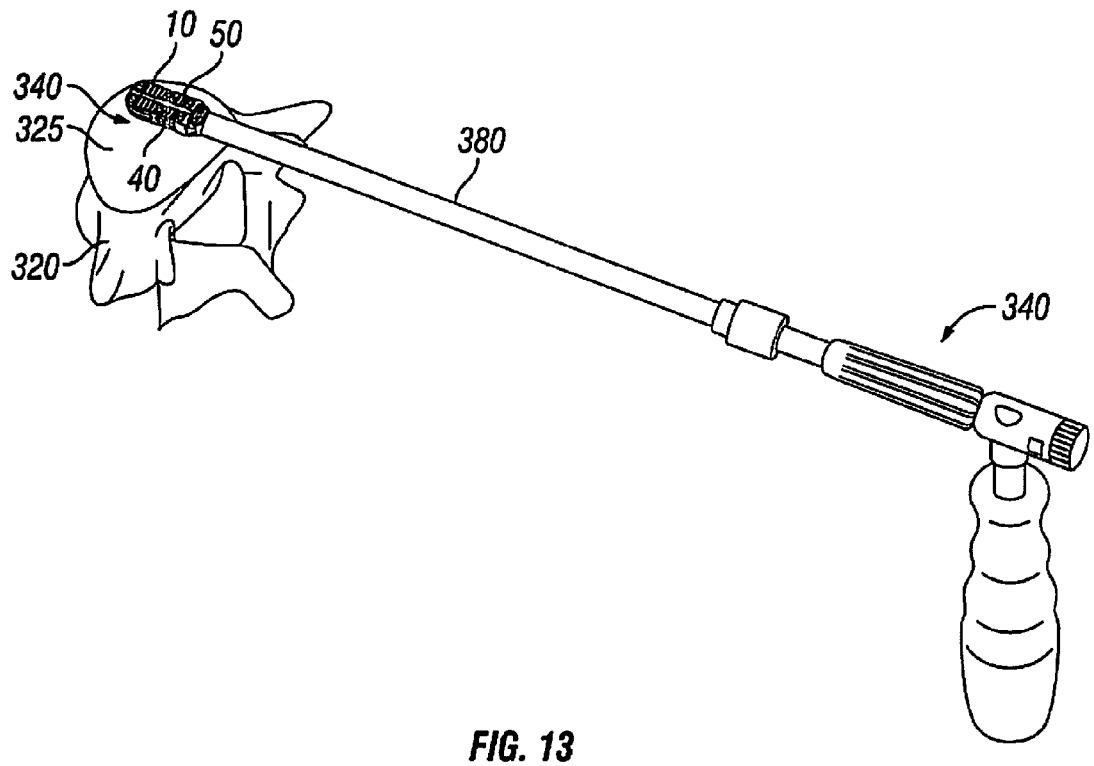
FIG. 13 is a view showing the tool of FIG. 12 introducing an expandable interbody spacer into a disc space in a collapsed position in accordance with embodiments of the present disclosure.
Figure 14:
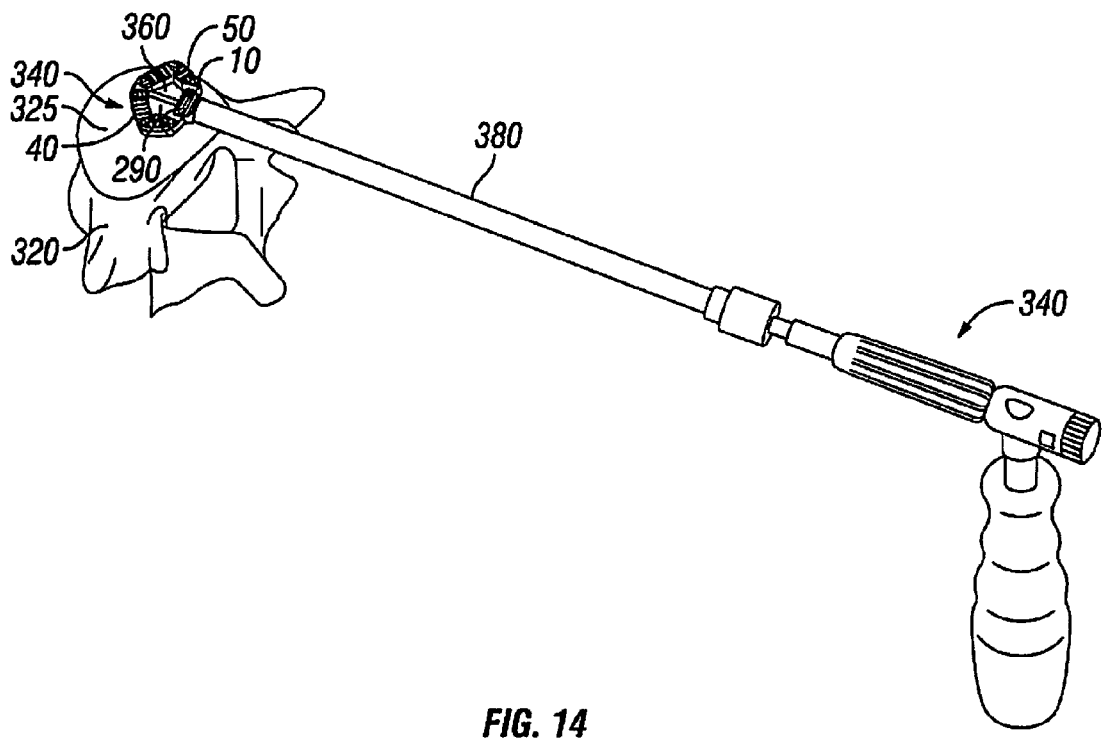
FIG. 14 is a view showing the tool of FIG. 12 expanding an expandable interbody spacer in a disc space in accordance with embodiments of the present disclosure.
Figure 15:
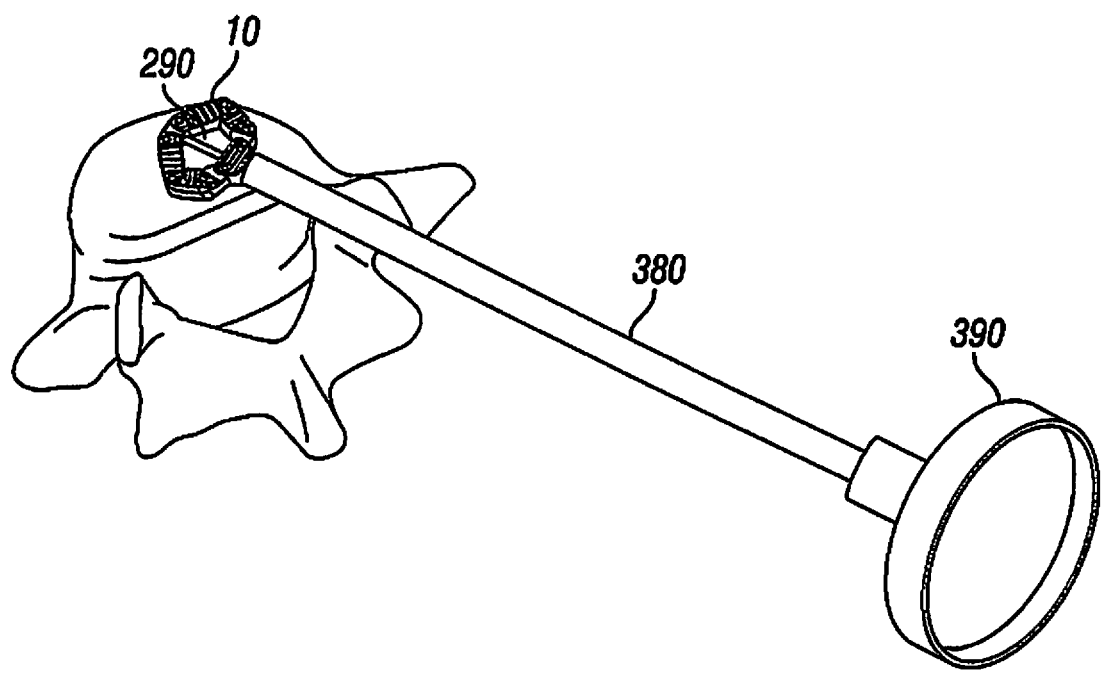
FIG. 15 is a view showing a funnel for introduction of bone-growth-inducing material into a disc space in accordance with embodiments of the present disclosure.

FIGS. 13 and 14 illustrate introduction of an expandable interbody spacer 10 into the disc space 330 using tool 340. For illustrative purposes, the upper vertebra 330 shown on FIG. 11 has been removed from FIGS. 13 and 14. As illustrated, the spacer 10 may be secured to the tool 340. For example, the elongated end portion 360 of the tool 340 may be disposed through the bore 270 (e.g., see FIG. 5) in the proximal connection end 60 with the distal tip 370 (e.g., see FIG. 12) of the end portion 360 secured in the opening 280 (e.g., see FIG. 5) in the distal connection end 70. As illustrated by FIG. 13, the tool 340 may introduce the spacer 10 into the disc space 330 through an access cannula 380. After introduction into the disc space 330, the spacer 10 may be laterally expanded. In accordance with present embodiments, the spacer 10 can be laterally expanded by folding the first arm 40 and the second arm 50 inward. By expanding laterally, the spacer 10 has an increased surface area contact with the endplate 325. In addition, the spacer 10 may engage harder bone around the apophyseal ring. As previously mentioned, an interior cavity 290 should be formed in the spacer 10 when in the expanded position. The tool 340 may then be detached from the spacer 10 and removed from the cannula 380. As illustrated by FIG. 15, a funnel 390 may then be placed on the cannula 380. Bone-growth inducing material may then be placed into the interior cavity 290 through the cannula 380. Because the spacer 10 has been laterally expanded, the interior cavity 290 should have a desirable amount of space for packing of the bone-growth-inducing material.

Figure 16:
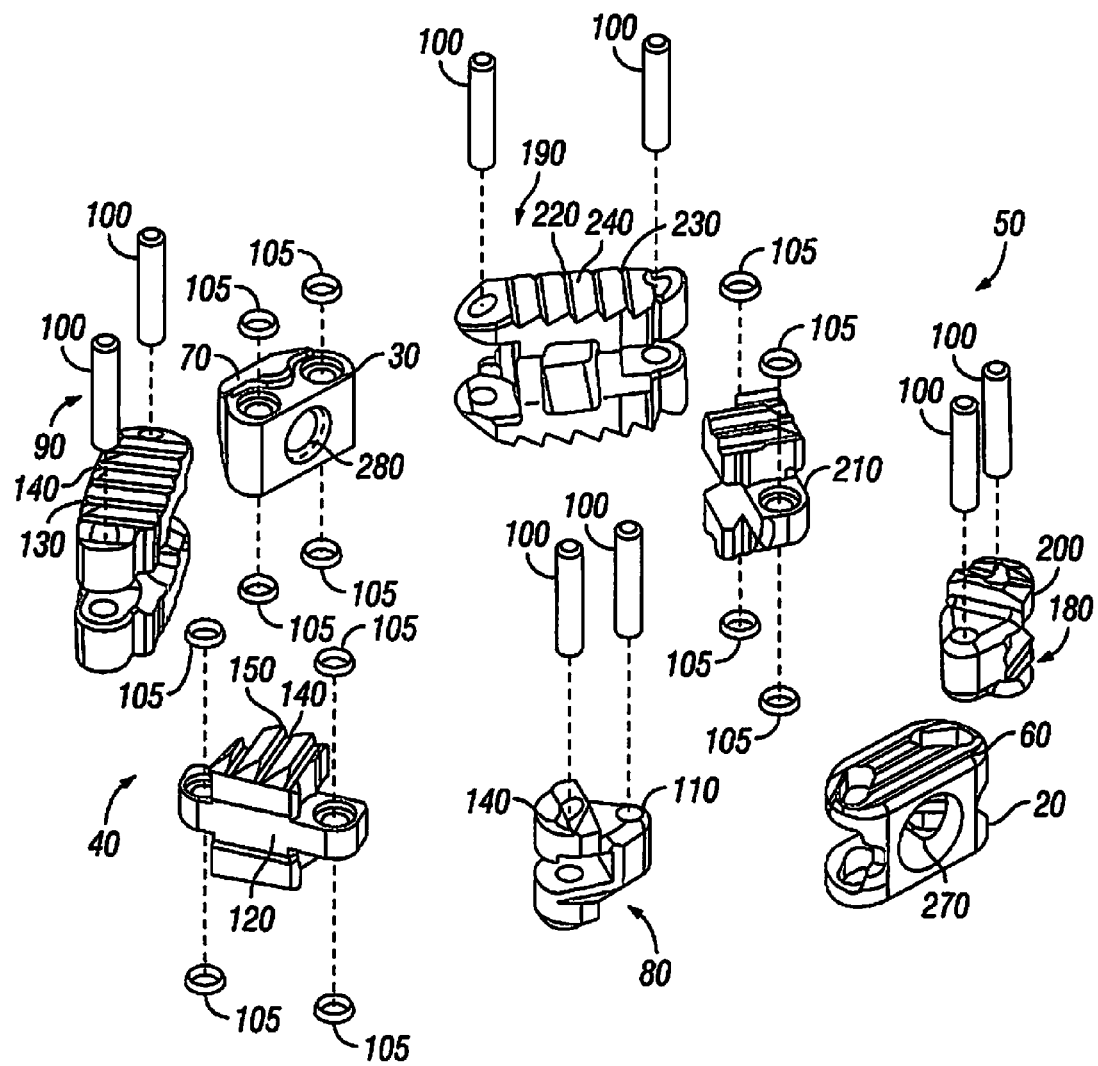
FIG. 16 is an exploded view of another embodiment of an expandable interbody spacer.

FIG. 16 illustrates an expandable interbody spacer 10 in accordance with an alternative embodiment. In the illustrated embodiment, the expandable interbody spacer 10 comprises a first jointed arm 40 and a second jointed arm 50. The first jointed arm 40 has a proximal end 80 and a distal end 90. The first jointed arm 40 comprises a plurality of links 110, 120, 130 connected end to end, for example, by pins 100. The first jointed arm 40 further may comprise washers 105 (e.g., PEEK washers) that may be disposed between the links 110, 120, 130 at their connections. The second jointed arm 50 has a proximal end 180 and a distal end 190. The second jointed arm 50 comprises a plurality of links 200, 210, 220 connected end to end, for example, by pins 100. The second jointed arm 50 further may comprise washers 105 (e.g., PEEK washers) that may be disposed between the links 200, 210, 220 at their connections. Washers 105 may also be disposed between the first arm 40 and the proximal connection member 60 and the distal connection member 70 at their respective connections. Washers 105 may also be disposed between the second arm 50 and the proximal connection member 60 and the distal connection member 70 at their respective connections. The washers 105 should have an interference fit to cause friction such that the spacer 10 may hold its shape in the entire range of the expanded implant.

Figure 18:
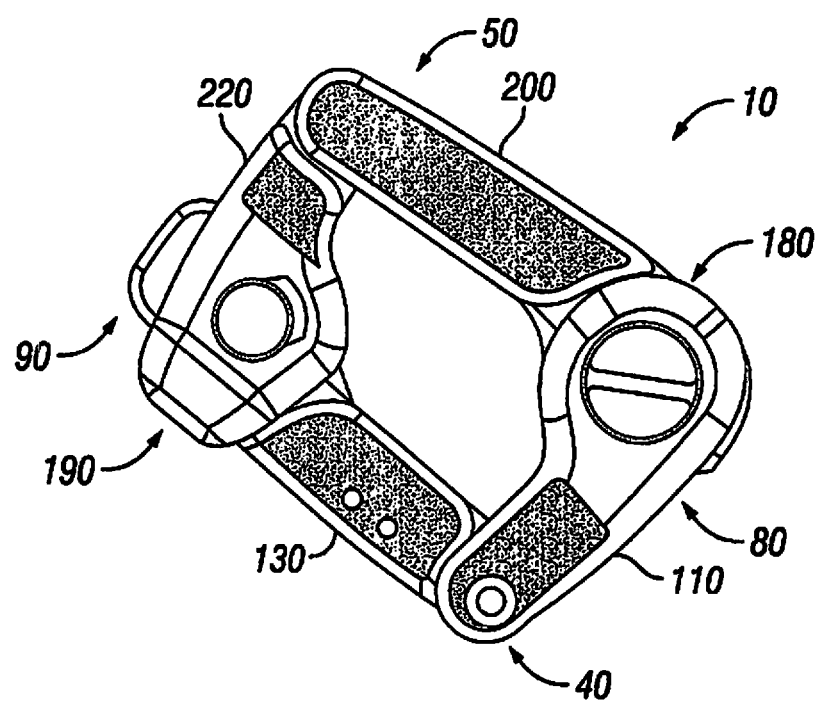
FIG. 18 is a top view of the expandable interbody spacer of FIG. 17 shown in an expanded position.
Figure 19:
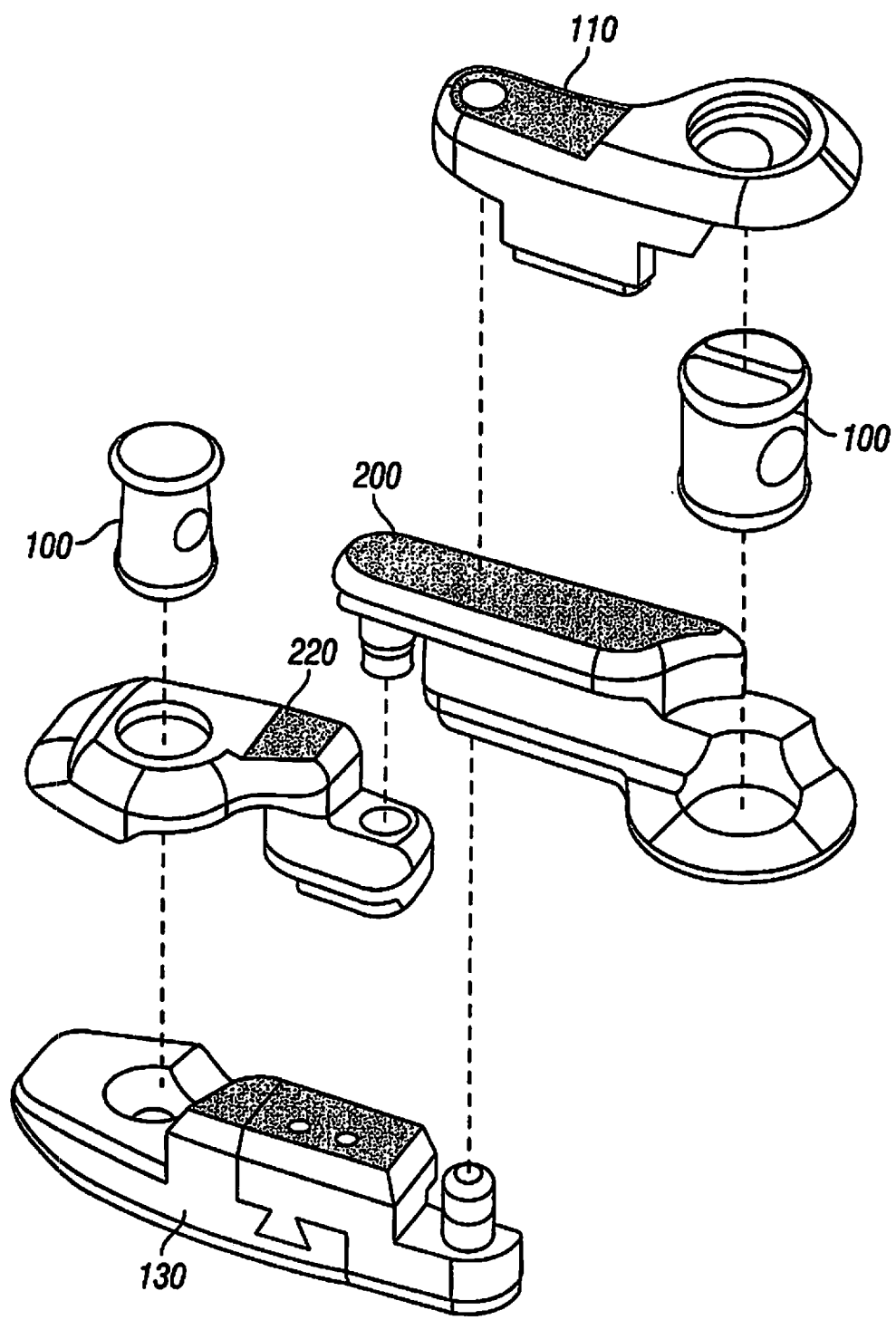
FIG. 19 is an exploded view of the expandable interbody spacer of FIG. 17.
Figure 20:
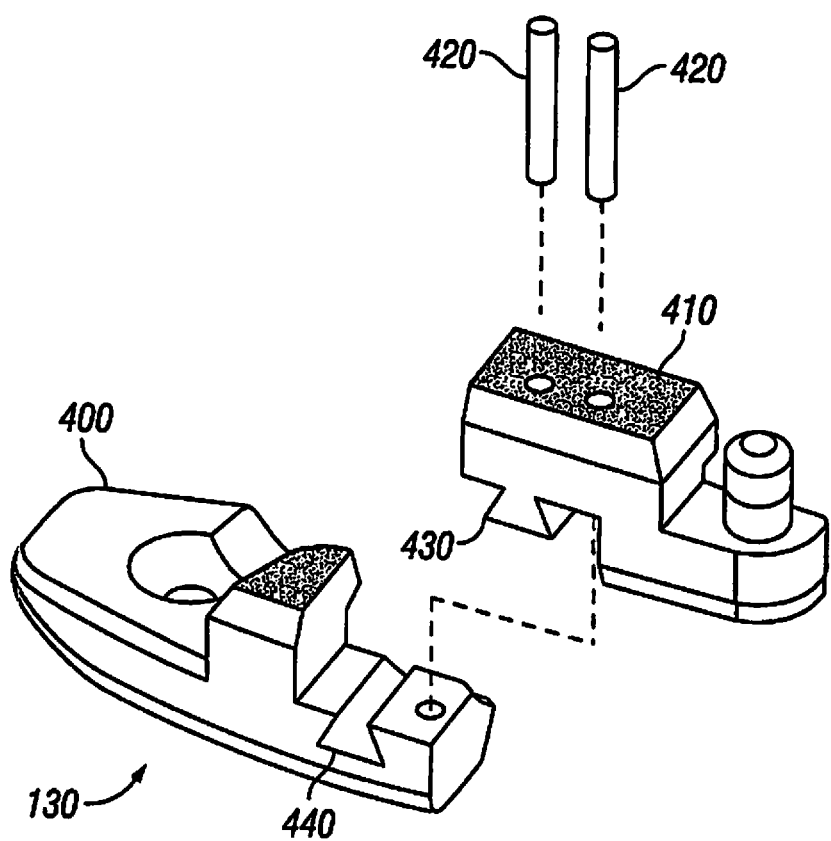
FIG. 20 is an exploded view of a link of a jointed arm of the expandable interbody spacer of FIG. 17.

The proximal ends 80, 180 may be pivotally coupled, for example, by pin 100, as shown on FIG. 19. The distal ends 90, 180 may also be pivotally coupled, for example, by pin 100, as shown on FIG. 19. The first jointed arm 40 comprises first link 110 and third link 130, the first link 110 and the third link 130 being pivotally coupled. In contrast to the first jointed arm 40 of FIGS. 1-10, there Referring now to FIGS. 17-19, an expandable interbody spacer 10 is illustrated in accordance with another embodiment of the present disclosure. In the illustrated embodiment, the expandable interbody spacer 10 comprises a first jointed arm 40 and a second jointed arm 50. The first jointed arm 40 has a proximal end 80 and a distal end 90. The second jointed arm 50 has a proximal end 180 and a distal end 190. The proximal ends 80, 180 may be pivotally coupled, for example, by pin 100, as shown on FIG. 19. The distal ends 90, 180 may also be pivotally coupled, for example, by pin 100, as shown on FIG. 19. The first jointed arm 40 comprises first link 110 and third link 130, the first link 110 and the third link 130 being pivotally coupled. In contrast to the first jointed arm 40 of FIGS. 1-10, there is no second link 120. As shown by FIG. 20, the third link 130 may comprise a first link segment 400 and a second link segment 410, which may be secured to one another by pins 420, for example. First link segment 400 and second link segment 410 may also have a tongue-and-groove connection, for example a groove 430 in the first link segment 400 may receive a tongue 440 of the second link segment 410. The second jointed arm comprises first link 200 and third link 220, the first link 200 and the third link 220 being pivotally coupled. In contrast to the second joint arm 50 of FIGS. 1-10, there is no second link 210.

Figure 17:
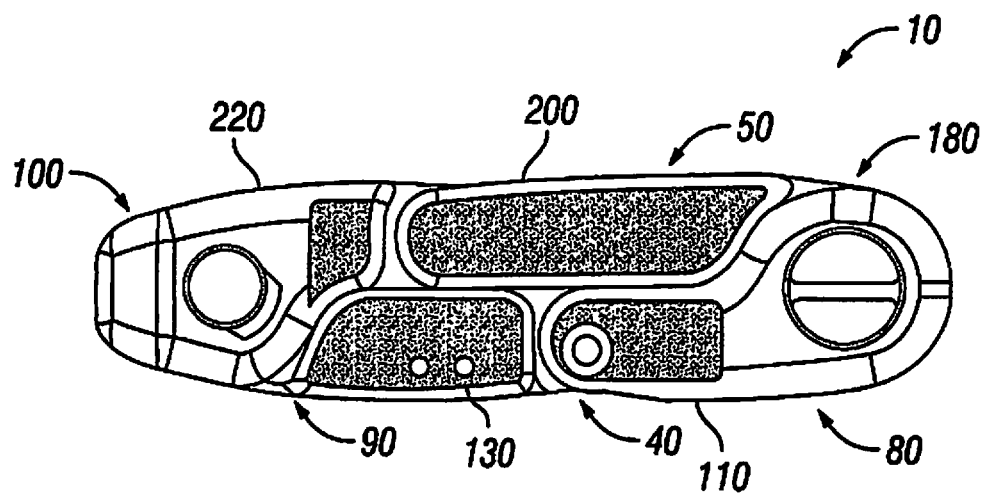
FIG. 17 is a top view of another embodiment of an expandable interbody spacer shown in a collapsed position.

In accordance with present embodiments, lateral expansion of the expandable interbody spacer 10 of FIGS. 17-19 may include folding the first arm 40 and the second arm 50 inward. For example, the proximal end 80 and the distal end 90 of the first arm 40 may be folded together, and the proximal end 180 and the distal end 190 of the second arm 50 may also be folded together.

Figure 21:
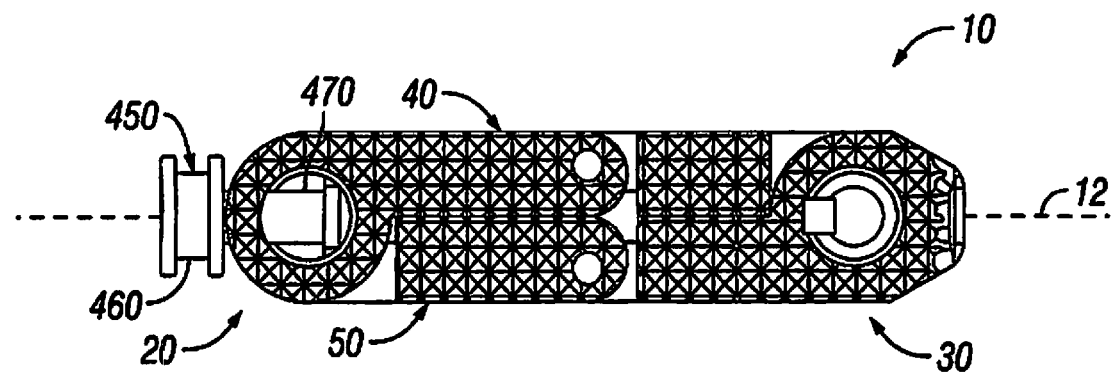
FIG. 21 is a top view of another embodiment of an expandable interbody spacer shown in a collapsed position.
Figure 22:
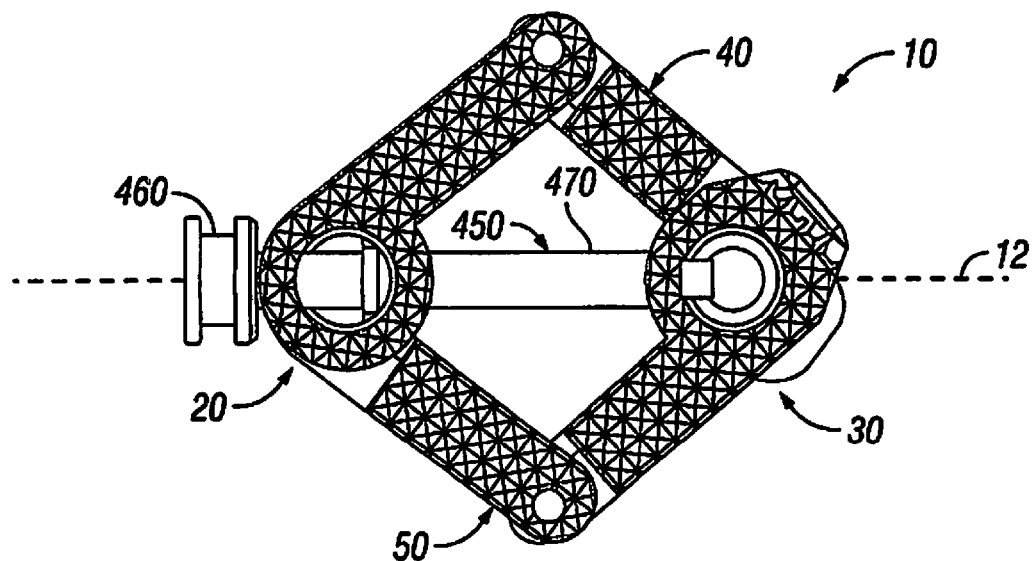
FIG. 22 is a top view of the expandable interbody spacer of FIG. 21 shown in an expanded position.

Referring now to FIGS. 21 and 22, an expandable interbody spacer 10 is illustrated in accordance with another embodiment of the present disclosure. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 12 of the spacer 10. As illustrated, the expandable interbody spacer 10 further may comprise an internal screw 450. The internal screw 450 may comprise a head 460 and an elongated body 470, which may extend generally parallel to the longitudinal axis 12 of the spacer 10. In some embodiments, the internal screw 450 may extend from the proximal end 20 to the distal end 30 of the spacer 10. In one embodiment, the elongated body 470 may be retractable. For example, the elongated body 470 may retract into the head 460, as shown on FIG. 22.

Figure 23:
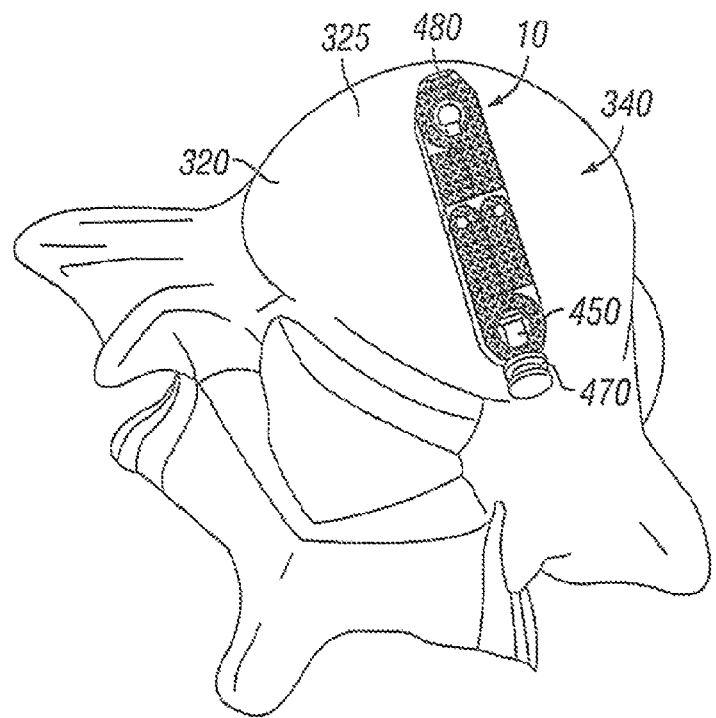
FIG. 23 is a view of the expandable interbody spacer of FIG. 21 shown in a disc space in a collapsed position.
Figure 24:
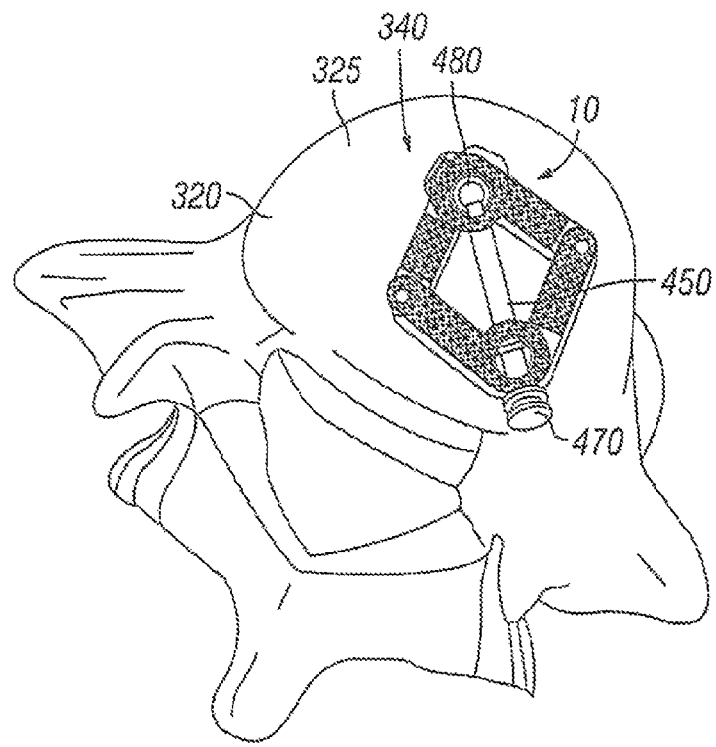
FIG. 24 is a view of the expandable interbody spacer of FIG. 21 shown in a disc space in an expanded position.

As illustrated by FIGS. 23 and 24, the spacer 10 may be introduced into the disc space 330, wherein the spacer 10 can be laterally expanded. In accordance with present embodiments, the spacer 10 can be laterally expanded by folding the first arm 40 and the second arm 50 inward. In some embodiments, the elongated body 470 may be retracted into the head 460 to cause folding of the first arm 40 and the second arm 50 inward, as the first arm 40 and the second arm 50 are secured to the distal end 480 of the internal screw 450.

Figure 25:
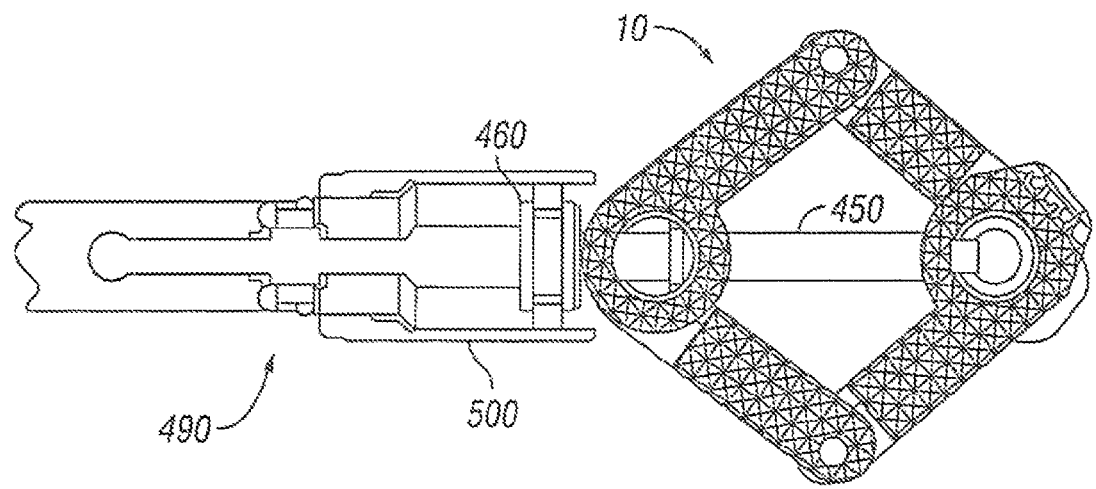
FIG. 25 is a top view of a tool shown engaging the expandable interbody spacer of FIG. 21 in accordance with embodiments of the present disclosure.
Figure 26:
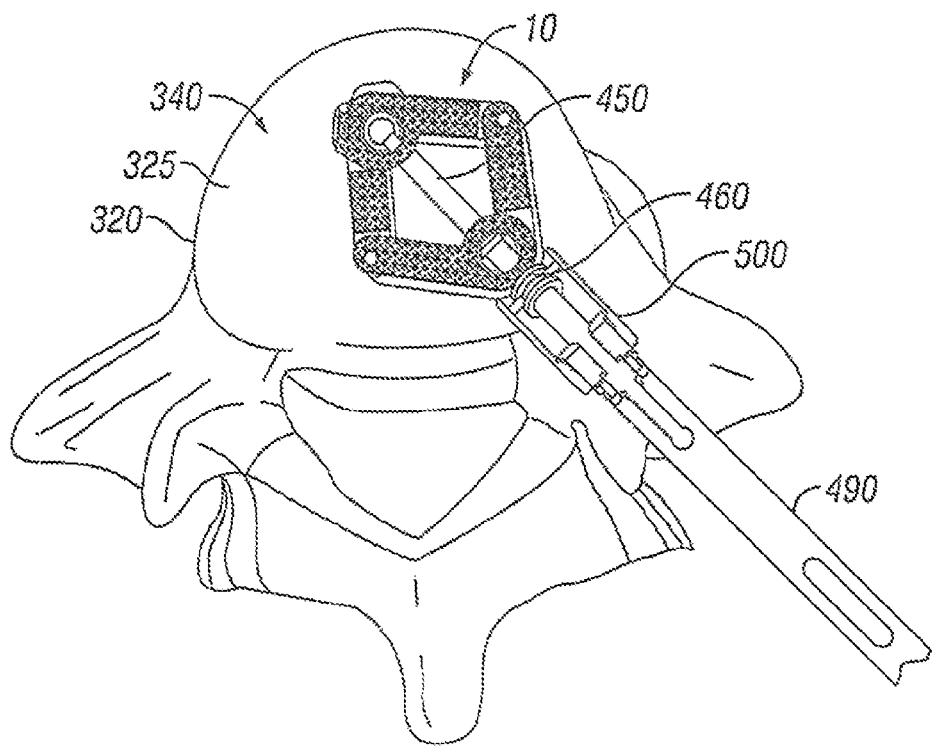
FIG. 26 is a view showing the tool of FIG. 24 expanding the expandable interbody spacer of FIG. 24 in a disc space in accordance with embodiments of the present disclosure.

FIG. 25 shows attachment of a tool 490 to the expandable interbody spacer 10 of FIGS. 22 and 23 in accordance with embodiments of the present disclosure. As illustrated, the tool 490 may have an attachment end 500, which can be secured to the head 460 of the internal screw 450. As shown by FIG. 26, the tool 40 can be used to introduce the spacer 10 into the disc space 330, wherein the spacer 10 can be laterally expanded.

Turning now to FIG. 27A-29, there are depicted multiple views of a further embodiment of an expandable interbody spacer 2700, in accordance with an aspect of the present disclosure. The expandable interbody spacer 2700 may include one or more features of any of the other interbody spacers discussed herein. For example, although the spacer 2700 and its components may be made of titanium, any suitable biocompatible material known in the art may be used.

Figure 27A:
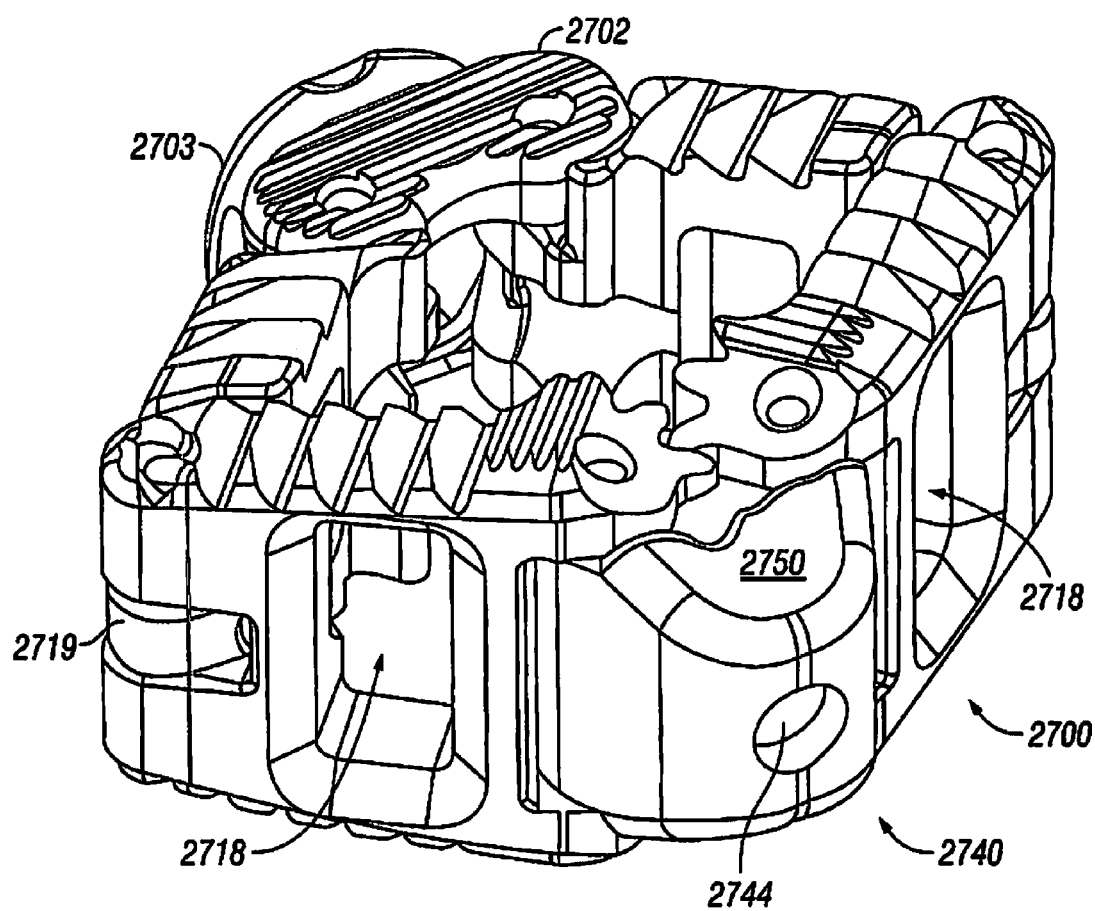
FIG. 27A is an isometric view of an exemplary expandable interbody spacer in an expanded position, in accordance with a further embodiment of the disclosure.
Figure 27B:
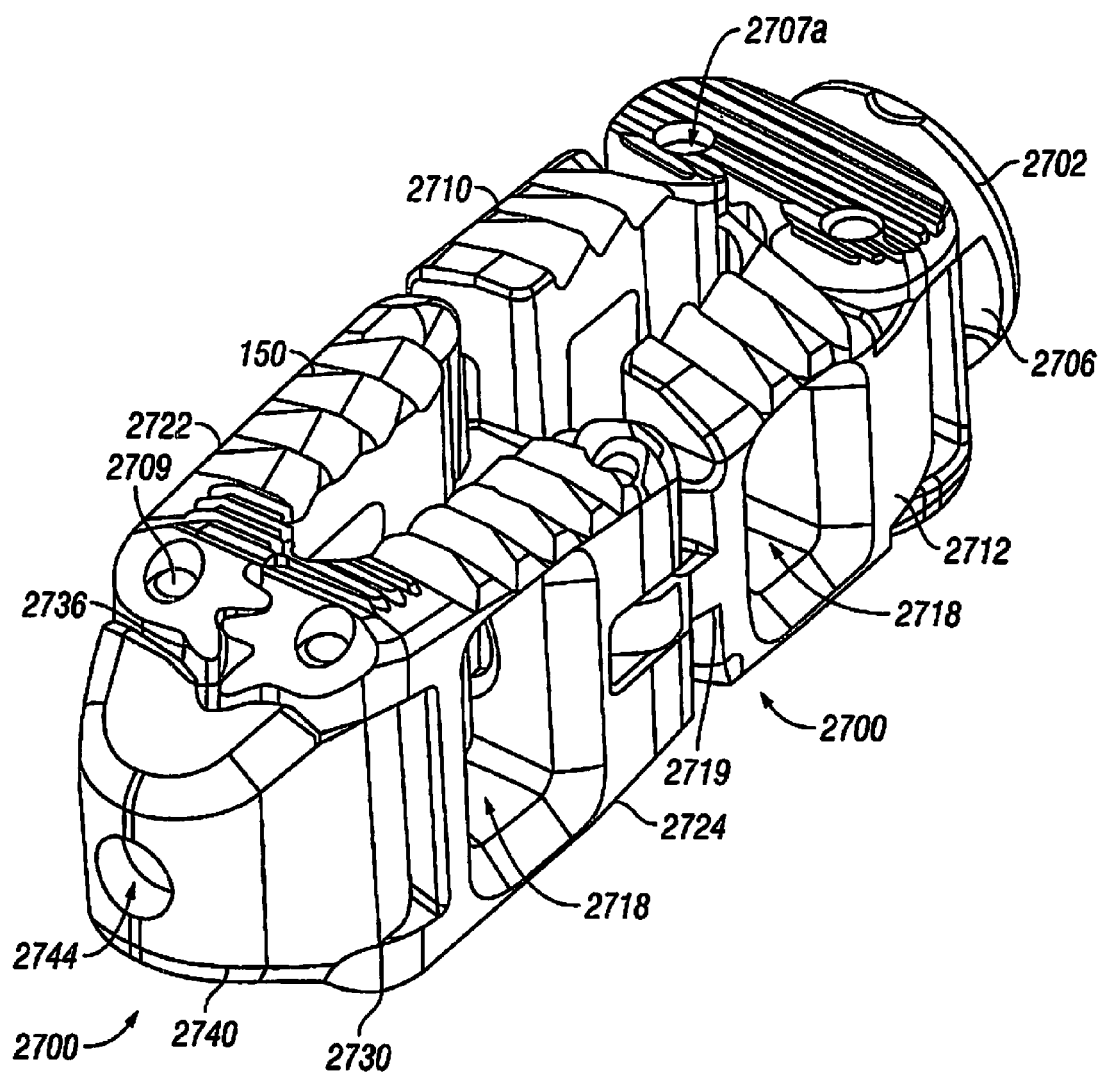
FIG. 27B is an isometric view of the expandable interbody spacer of FIG. 27A in the collapsed position.

With reference to FIG. 27A, for example, spacer 2700 may include, among other things, a proximal portion 2702. Proximal portion 2702 may include a substantially cylindrical portion 2703. Cylindrical portion 2703 may include a complete cylindrical shape or a partial cylindrical shape. In addition, cylindrical portion 2703 may define a lumen 2704 therethrough. A surface of the lumen 2704 may include one or more geometric features, such as, for example, screw threads 2705, as described in greater detail below. In one embodiment, lateral surfaces of cylindrical portion 2703 may include one or more geometric features 2706 to facilitate engagement by a tool 3000, as discussed below in greater detail. The geometric features 2706 may include any suitable shape and/or configuration. In one embodiment, the geometric features 2706 may include elongate notches disposed in the side walls that define cylindrical portion 2703. Further, the elongate notches may extend into the side walls in a direction that is substantially perpendicular.

A plurality of cantilevered ledges 2707 may extend distally from a distal portion of cylindrical portion 2703. Aside from being disposed in an opposing relation to one another, the cantilevered ledges 2707 may be substantially similar to one another. The ledges 2707 may include any suitable configuration, shape, and/or size known in the art. In one embodiment, the ledges 2707 may define a space 2708 therebetween for receiving a plurality of links (as described below) of spacer 2700. External surfaces (e.g., inferior and superior surfaces) of ledges 2707 may include texturing 150 to aid in gripping adjacent vertebral bodies, as described herein. The external surfaces may also be configured to promote bone ingrowth. For example, in one embodiment, the external surfaces of ledges 2707 may include a porous configuration or may include a coating of, e.g., hydroxyapatite. External edges of ledges 2707 may include any suitable configuration for matingly coupling with corresponding portions of the plurality of links discussed below. In one embodiment, the external edges of ledges 2707 may be curved to facilitate the plurality of links pivoting relative to each of ledges 2707. Further, each of ledges 2707 may include one or more openings 2707a for receiving a pivot pin 2709 therethrough, as described below in greater detail.

With continued reference to FIGS. 27A-29, proximal portion 2702 may be rotatably coupled via a plurality of pivot pins 2709 to links 2710 and 2712. Links 2710 and 2712 may be substantially similar to one another. Indeed, as depicted in, e.g., FIG. 27A, links 2710 and 2712 may be positioned as mirror images of each other. Thus, for the purposes of brevity, similar portions of links 2710 and 2712 will be described together. Proximal portions 2714 of links 2710 and 2712 may be received in space 2708. The proximal portions 2714 of links 2710, 2712 may be appropriately configured and dimensioned to fit between ledges 2707. In addition, each of proximal portions 2714 includes a through-hole 2716 for receiving a pivot pin 2709. The through-hole 2716 may be disposed in a scalloped cut-out on proximal portions 2714 of each of links 2710, 2712.

Pivot pin 2709 may include any suitable fastener known in the art for movably coupling links 2710 and 2712 to proximal portion 2702. In one embodiment, pivot pin 2709 may be inserted and retained within openings 2707a and through-holes 2716 via an interference or friction fit.

In some embodiments, an interface between one or both of links 2710 and 2712 and proximal portion 2702 may be configured to retain one or both of links 2710 and 2712 in a predetermined position relative to proximal portion 2702. For example, an edge of ledge 2707 may interact with a wall 2717 to frictionally retain in a predetermined position relative to proximal portion 2702. In one embodiment, the wall 2717 may include a raised portion (not shown), such as, e.g., a rounded bump, or other suitable feature against which the edge of ledge 2707 may engage.

Superior and inferior surfaces of links 2710 and 2712 may also include suitable texturing 150 as described above. In addition, the superior and inferior surfaces may be configured to promote bone ingrowth, as described above. Each link 2710 and 2712 also may define one more openings 2718 therethrough. The openings 2718 may include any suitable configuration known in the art. In one embodiment, openings 2718 may include a substantially rectangular configuration. In other embodiments, openings 2718 may include other shapes. In one embodiment, the openings 2718 may be disposed distally of wall 2717. Openings 2718 may be configured as bone graft windows, allowing facilitating bone ingrowth into an interior of spacer 2700 through openings 2718 An edge of opening 2718 may be appropriately beveled, chamfered, and/or rounded, as is known in the art. Further, opening 2718 may be generally disposed in a central portion of each of links 2710 and 2712.

A distal end portion of links 2710, 2712 may be configured to be movably coupled to another link, as discussed herein. In one embodiment, the distal end portions of links 2710, 2712 may define a male hinge 2719 that includes a hole 2720 therethrough. The hole 2720 may be configured to receive a pivot pin 2709 for rotatable coupling the links 2710, 2712 to adjacent links described below. In one embodiment, a wall perpendicular to hinge 2719 may define one or more position retaining features 2721. As will be described below, the position retaining features 2721 may be configured to interact with corresponding features on an adjacent link to frictionally retain links in a predetermined position.

The ends of each of links 2710, 2712 that are opposite to the ends coupled to proximal portion 2702 may be movably coupled to links 2722 and 2724. Each of links 2722 and 2724 may be substantially similar to one another. Thus, those of ordinary skill in the art will understand that either link 2722 or link 2724 may include features of the other link 2722 or link 2724. A proximal end portion of each of links 2722 and 2724 may define a recess 2725 for receiving hinge 2719. The recess 2725 may be disposed between a pair of proximally extending arms 2725*a* and 2725*b*. Each of arms 2725*a*, 2725*b* may be substantially similar to one another and, thus, for the purposes of efficiency, only one arm 2725*a* will be discussed.

Arm 2725*a* may include any suitable shape and/configuration known in the art. In one embodiment, an external surface of arm 2725*a* may be rounded to facilitate rotating relative to link 2712 or 2710. A lateral surface of arm 2725*a* may include one or more position retaining features 2727 for engaging position retaining features 2721. In use, as links 2724 and 2712 may rotate relative to one another, for example, position retaining features 2721 and 2727 may frictionally engage one another to retain links 2724 and 2712 in a desired position. Position retaining features 2727 may be similar to position retaining features 2721. For example, in one embodiment, position retaining feature 2727 may be a bump that is raised relative to a remaining surface of arm 2725*a*.

Each link 2722 and 2724 may also include one or more openings 2718 disposed generally in a central portion of links 2722 and 2724. As discussed above, openings 2718 may be configured to extend through each respective link 2722, 2724, and may be configured to facilitate bone-ingrowth. One or more edges of openings 2718 may be beveled, rounded, and/or chamfered as known in the art.

A distal end of each link 2722 and 2724 may include a plurality of extensions 2729, 2730. Extensions 2729, 2730 may be configured to extend away from a central portion of the links 2722, 2724, and may be configured to define a space 2732 therebetween. The space 2732 may be configured to receive a distal component of spacer 2700. Each of extensions 2729, 2730 may include a through-hole 2734 therein. The through-hole 2734 may include any suitable configuration known in the art. The through-hole 2734 may be configured to receive a respective pivot pin 2709 for movably coupling links 2722, 2724 to the distal component discussed in greater detail below.

Figure 28:
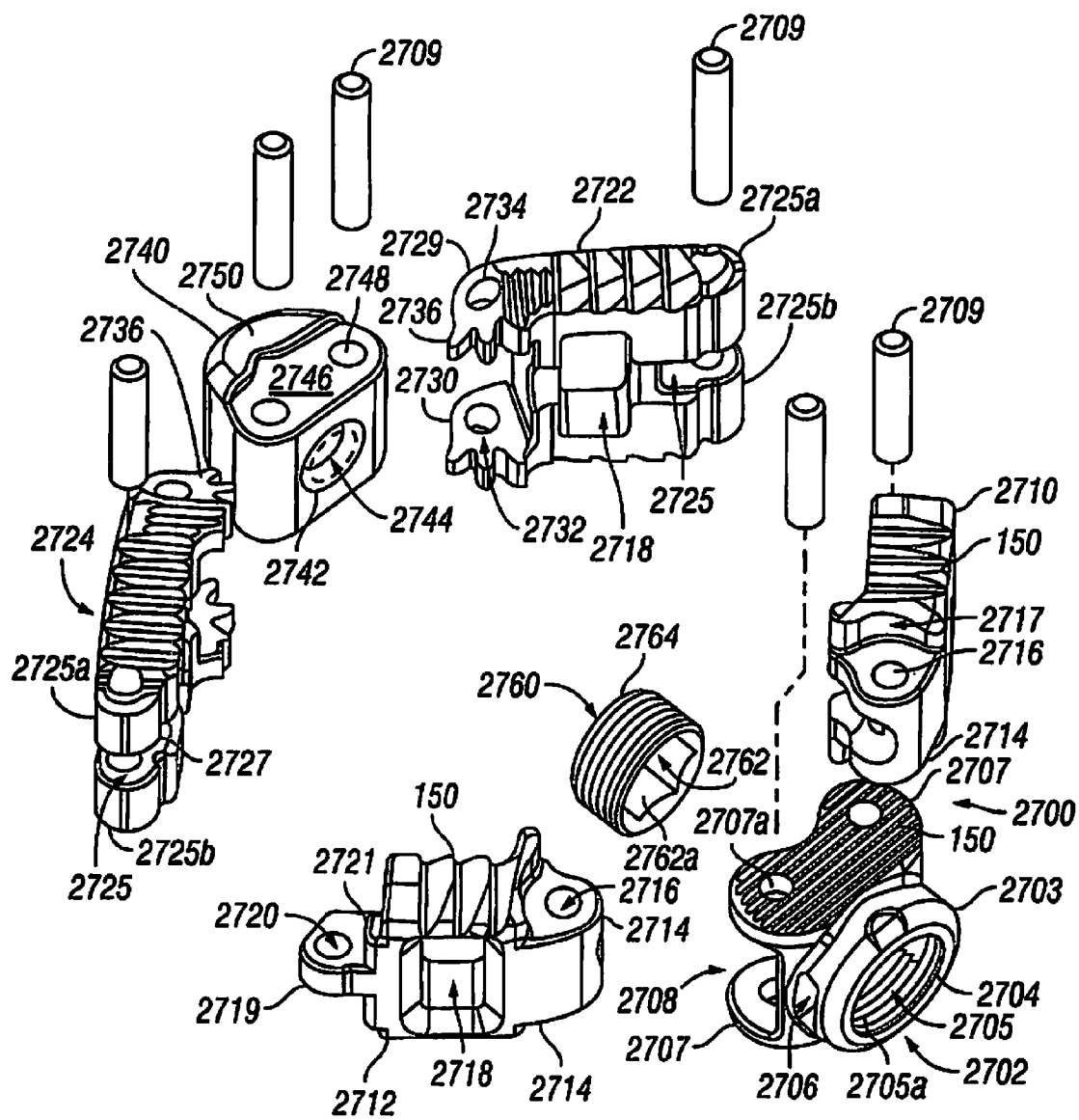
FIG. 28 is an exploded view of the expandable interbody spacer of FIG. 27A.

Inward facing surfaces of one or both of extensions 2729, 2730 may be configured to interact or engage with corresponding surfaces of the extensions 2729, 2730 of an opposing link. For example, as shown in FIG. 28, the inward facing surfaces of extensions 2729, 2730 of one of links 2722, 2724 may include a plurality of teeth, recesses, protrusions, notches, or the like, that may be configured to engage corresponding geometry disposed on the inward facing surfaces of the extensions disposed on the other of links 2722, 2724. In the preferred embodiment, the inward facing surfaces of extensions 2729, 2730 may include a plurality of gear teeth 2736. The gear teeth 2736 of each extension 2729, 2730 may engage gear teeth 2736 of the opposing link to facilitate rotating one link relative to the other in a single plane.

Each of links 2722 and 2724 may be movably coupled to a distal component 2740. Distal component 2740 may include a substantially trapezoidal configuration. That is, distal component 2740 may taper in the distal direction from a larger width dimension to a smaller width dimension. With reference to FIG. 28, a proximal face of distal component 2740 may include an opening 2742 in communication with a hole 2744 through distal component 2740. As shown in, e.g., FIG. 27A, hole 2744 extends completely through distal component 2740. Hole 2744 may include any suitable configuration known in the art. In one embodiment, hole 2744 may include a substantially conical configuration as it tapers towards a smaller diameter in its distal portion. As will be discussed below, hole 2744 may include internal threads for engaging with an implantation tool.

Superior and inferior surfaces of distal component 2740 may be configured to receive extensions 2729, 2730. Accordingly, as best shown in FIG. 28, for example, these surfaces may include a stepped portion 2746 for receiving extensions 2729, 2730 of each link 2722, 2724. Stepped portion 2746 may include a plurality of openings 2748 for receiving a pivot pin 2709 therein to rotatably couple the links 2722, 2724 to distal component 2740. Those of ordinary skill in the art will understand that links 2722, 2724 may be coupled to distal component 2740 by any suitable means known in the art. Distal component 2740 may include a raised portion disposed distally of stepped portion 2746. The raised portion 2750 may include any suitable configuration known in the art. In one embodiment, the raised portion 2750 may include a distally tapering configuration, as shown in FIG. 27A. As also shown in FIG. 27A, distal component 2740 may include a curved external configuration.

Figure 29:
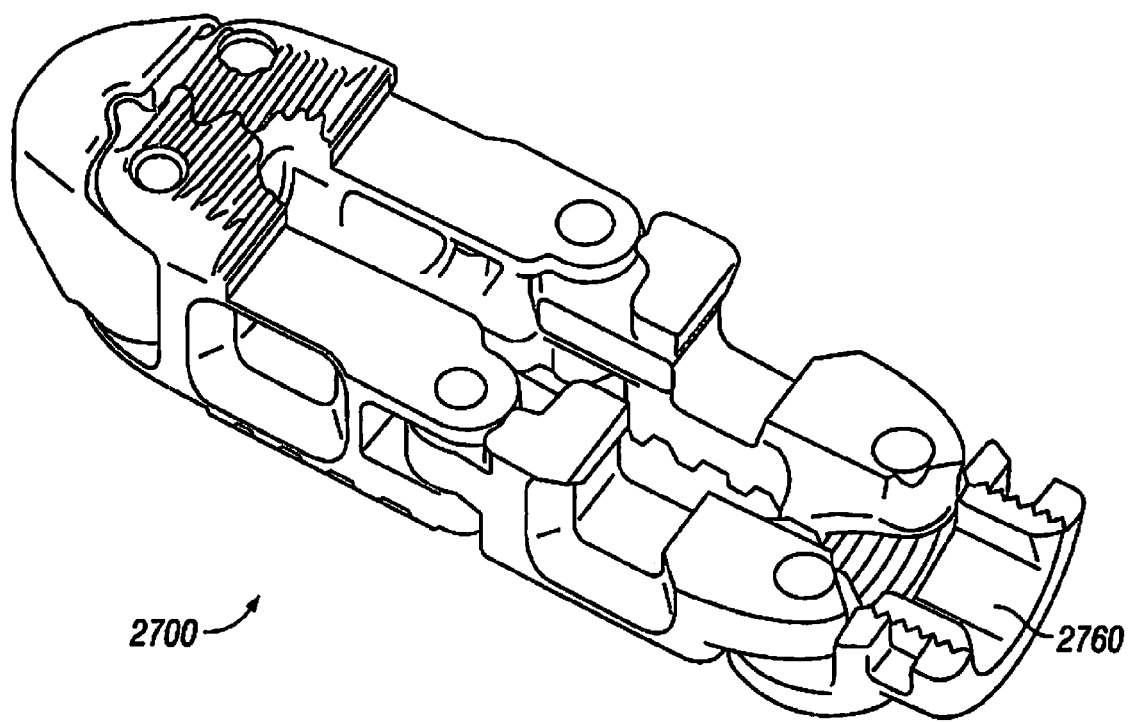
FIG. 29 depicts a cross-sectional view of the expandable interbody spacer of FIG. 27A in the collapsed position.

With reference now to FIGS. 28-29, the spacer 2700 may be maintained in an expanded configuration (shown in FIG. 27A) by any suitable mechanism known in the art. As discussed above, the spacer 2700 may include certain position retaining features. To more permanently retain an expanded configuration of spacer 2700, the spacer 2700 may include a locking feature 2760. Those of ordinary skill in the art will understand that locking feature 2760 may include any suitable configuration known in the art. In one embodiment, locking feature 2760 may include a substantially cylindrical configuration. In addition, locking feature 2760 may define a lumen 2762 therethrough. In one embodiment, the walls of the lumen 2762 may include a plurality of geometric configurations 2762*a* to allow a tool (described in greater detail below) to engage and rotate locking feature 2760. Further, locking feature 2760 may be configured and dimensioned to be received within lumen 2704 of proximal portion 2702, as shown in FIG. 29. In one embodiment, an external surface of locking feature 2760 may include suitable geometric features for engaging lumen 2704. In the embodiment where lumen 2704 includes threads 2705, the external surface of locking feature 2760 may include corresponding threads 2764. The threads 2705 in lumen 2704 and threads 2764 may cooperate to only allow locking feature 2760 to be advanced into lumen 2704 without being withdrawn, regardless of whether locking feature is rotated clockwise or counter-clockwise. For example, in one embodiment, threads 2705 may terminate short of the opening to lumen 2704. In addition, or alternatively, one or more raised circumferential or partially circumferential protrusions 2705*a* may be formed just inside of the opening to lumen 2704. In such embodiments, locking feature 2760 may be pre-disposed within lumen 2704 during a manufacturing or assembly process and before delivery to a user or healthcare professional. Thus, the user or healthcare professional is only able to rotate locking feature 2762 to advance it further into lumen 2704 and is unable to remove locking feature 2762 from 2704.

With reference to FIG. 29, and as will be discussed in greater detail below, locking feature 2760 may be configured to be advanced into lumen 2704 and protrude out of cylindrical portion 2703 into space 2708, which, as shown in FIG. 29, is occupied by proximal portions 2714 of links 2710 and 2712 when the spacer 2700 is in the collapsed configuration. When the spacer 2700 is in the expanded position, the proximal portions 2714 may be moved out of the space 2708. Accordingly, locking feature 2760 may be rotated and consequently advanced further into lumen 2704 so that a distal portion of locking feature 2760 extends out of lumen 2708 and into the space 2704. In this position, the locking feature 2762 may be configured to prevent links 2710 and 2712 from returning to their collapsed positions.

The components of spacer 2700 may be fabricated from any suitable material known in the art, including, but not limited to those described above. In one embodiment, one or more components of spacer 2700 may be fabricated from titanium. Further, portions of spacer 2700 may include any suitable coating known in the art, including, but not limited to, coatings of suitable therapeutic, antiseptic, anesthetic, and/or antibiotic. In addition, as alluded to above, portions of spacer 2700 may be configured to promote bone ingrowth into the structure of spacer 2700.

Figure 30:
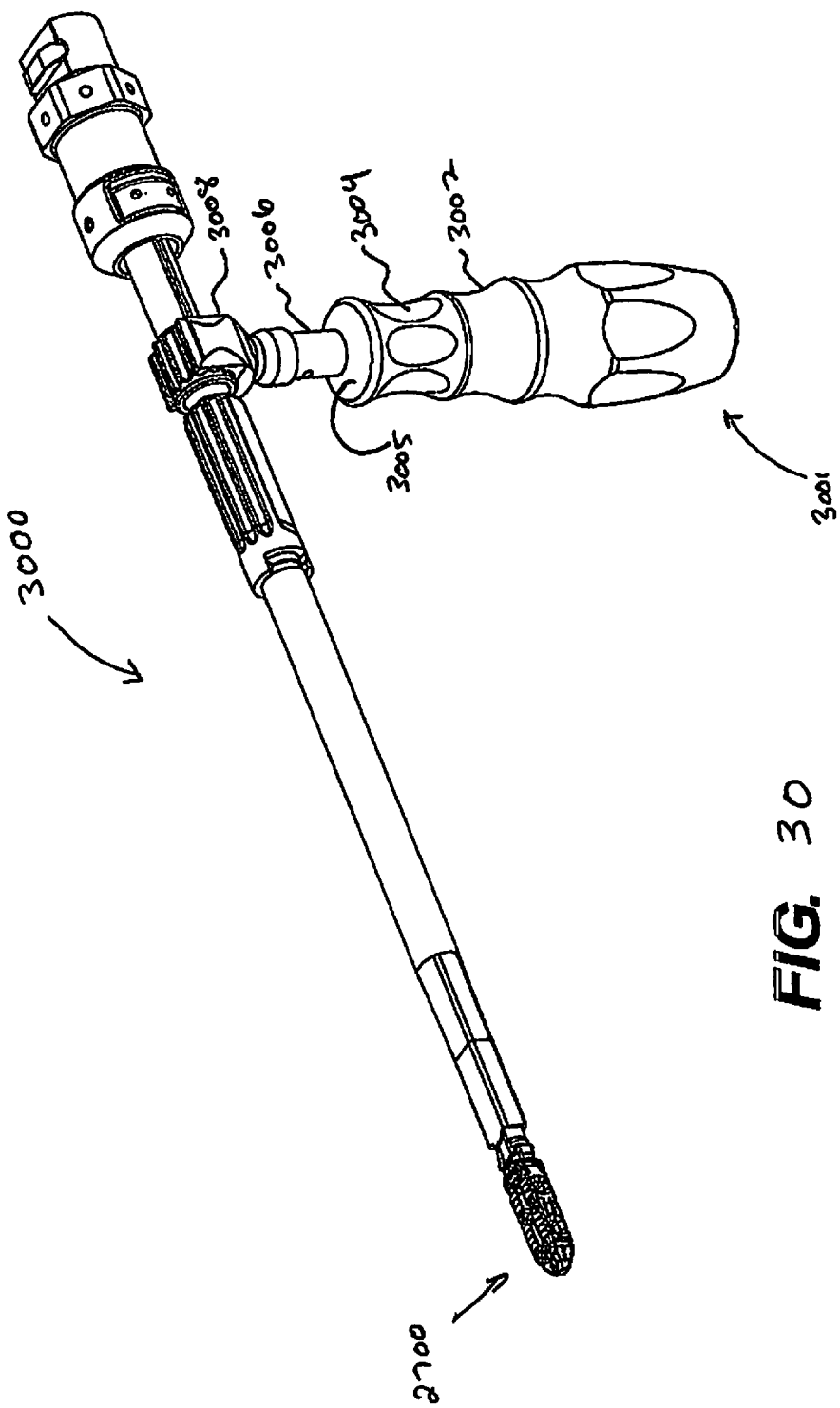
FIG. 30 depicts an embodiment of an exemplary tool for implanting an embodiment of an exemplary expandable interbody spacer, in accordance with the principles of the present disclosure.
Figure 31:
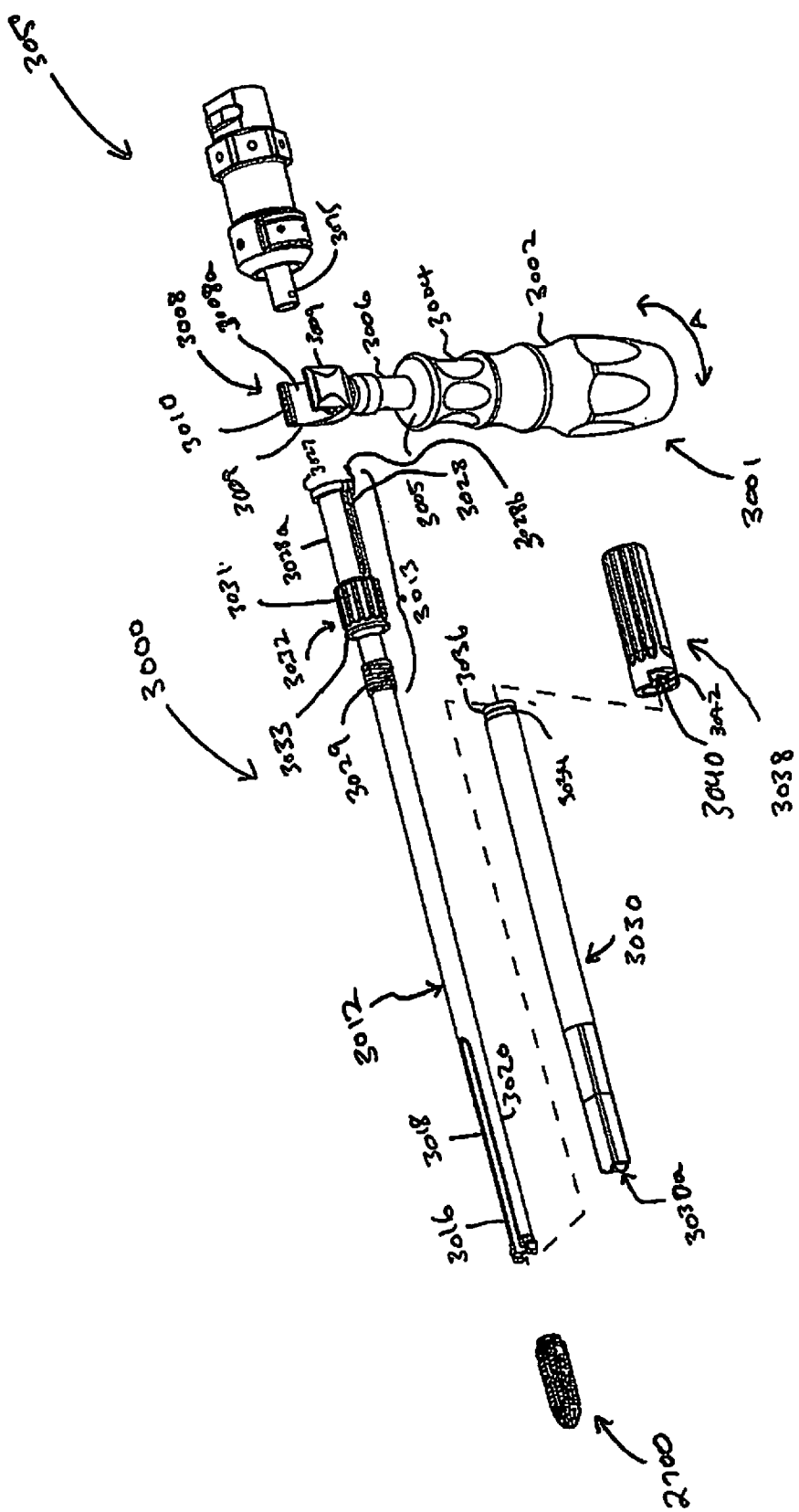
FIG. 31 depicts a partially-exploded view of various components of the tool shown in FIG. 30.

Turning now to FIGS. 30-31, there is depicted an exemplary embodiment of a tool 3000 for effecting implantation, removal, and otherwise manipulation of the various embodiments of expandable interbody spacers described herein. Tool 3000 may include a plurality of components, each of which will be discussed in greater detail below. Those of ordinary skill in the art will recognize that any of the individual components discussed herein may be combined with other components or may be omitted altogether without departing from the principles of the present disclosure.

Tool 3000 may include a handle assembly 3001. Handle assembly may include an elongate structure 3002 configured to be held in the hand of an operator or healthcare professional. As such, the elongate structure 3002 may be appropriately configured and dimensioned as is known in the art. In some embodiments, elongate structure 3002 may include a plurality of geometric configurations or features 3004, such as, e.g., bumps, grooves, indentations, ridges, knobs, cut-outs, etc. for gripping by an operator. In addition, elongate structure 3002 may include a constant cross-sectional dimension throughout its length, or elongate structure 3002 may include varying dimensions throughout its length. Further, elongate structure 3002 may include a substantially circular cross-sectional configuration. In some embodiments, however, elongate structure 3002 may include any suitable cross-sectional configuration, including, but not limited to, square, rectangular, triangular, etc.

A generally cylindrical extension member 3006 may extend away from a superior surface 3005. For the purposes of FIGS. 30-31 only, the orientation depicted is presumed to be an orientation during operation. Thus, terms such as "superior," "anterior," "proximal," "distal," "inferior," and "posterior" are used relative to this orientation. The extension member 3006 may serve to rotatably connect elongate structure 3002 to holder 3008.

Holder 3008 may include any suitable configuration known in the art. In one embodiment, holder 3008 may be configured, shaped, and sized to receive and frictionally engage a proximal portion of an inserter fork described in greater detail below. In one embodiment, for example, holder 3008 may include a substantially U-shaped configuration. The inserter fork may be received with the "U" portion 3008a of the holder 3008. The U-shaped holder 3008 may include a base portion, and two superiorly extending arms 3009. One or more of arms 3009 may be provided with one or more geometric features for frictionally engaging and retaining the inserter fork. For example, the geometric features may include dents, indents, recesses, apertures, protrusions, ribs, and the like. In one embodiment, an inner surface of an upper portion of each arm 3009 may include a rib 3010. In some embodiments, the U-shaped holder 3008 may include a securing member for retaining (by, e.g., friction) the inserter fork within holder 3008. In one embodiment, the securing member may be selectively actuatable. For example, the base portion of the holder 3008 may include a set screw (not shown) or other similar mechanism that may selectively engage a portion of the inserter fork to retain the inserter fork relative to the holder 3008. The set screw may be configured to transition between a first configuration and a second configuration. In the first configuration, the set screw may be received substantially completely or completely within the base portion of holder 3008. In the second configuration, the set screw may be advanced out of the base portion 3008 and into the "U" portion 3008a. The set screw may be configured to transition between the first and second configurations by rotating elongate structure 3002 relative to holder 3008 in the directions shown by arrow A. For example, rotating elongate structure 3002 may rotate a head (not shown) of the set screw, thereby advancing the set screw out of the base portion of holder 3008.

Figure 32A:
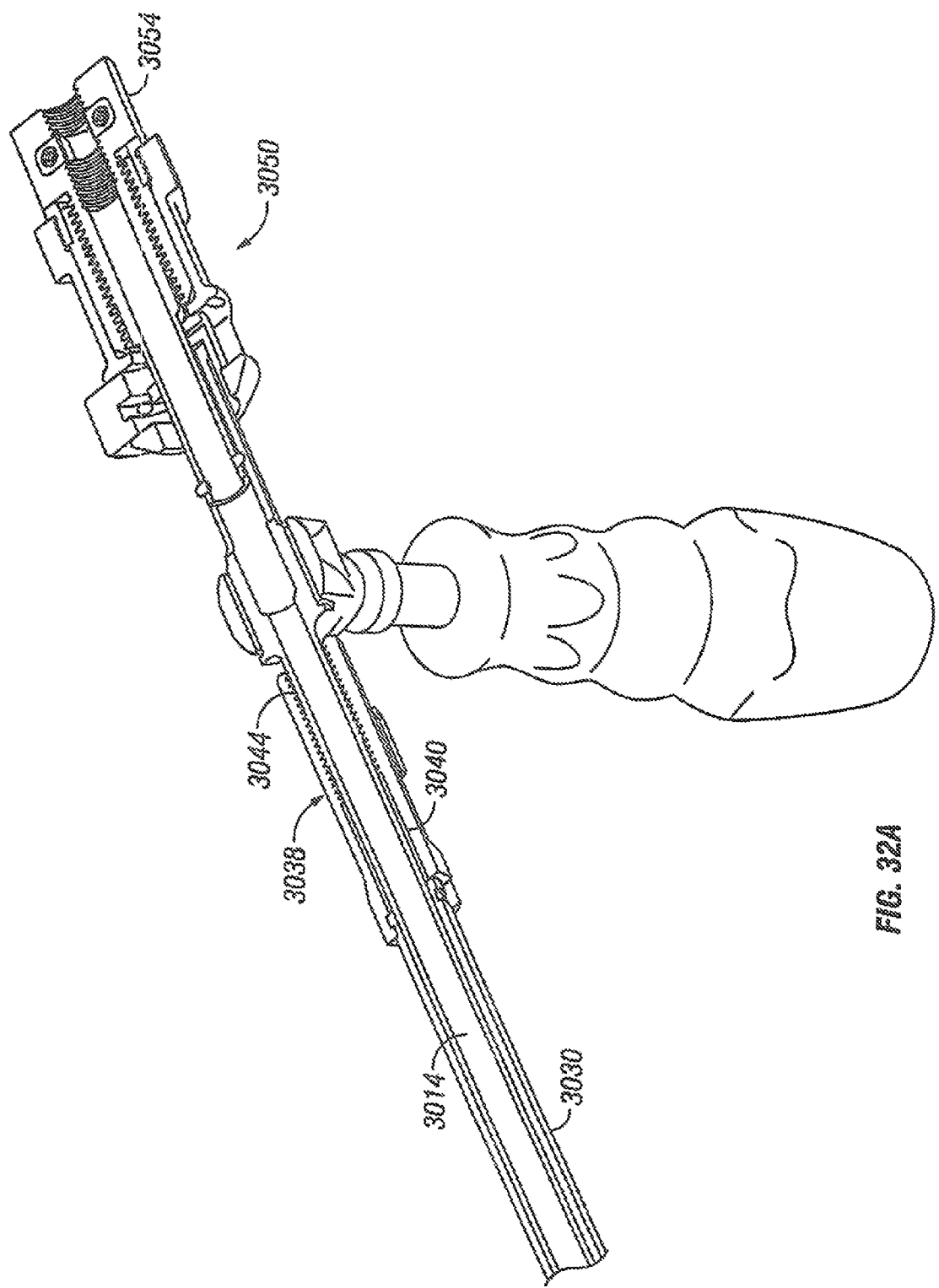
FIG. 32A depicts a cross-sectional view of a proximal portion of the tool of FIG. 30.

With continued reference to FIG. 31, the inserter fork may include a generally elongate structure 3012. In some embodiments, the elongate structure 3012 may define one or more lumens therein. For example, as shown in FIG. 32A, the elongate structure 3012 may define a lumen 3014 therethrough. Elongate structure 3012 may include any suitable cross-sectional structure known in the art. For example, in some embodiments, the elongate structure 3012 may be a generally tubular structure. In other embodiments, elongate structure 3012 may include a substantially rectangular cross-sectional configuration. In a further embodiment, the cross-sectional configuration of elongate structure 3012 may vary along its length. For example, as shown in FIG. 31, a distal portion of elongate structure 3012 may include a substantially square or rectangular cross-sectional configuration and a proximal portion of elongate structure 3012 may include a substantially circular cross-sectional configuration.

Figure 33:
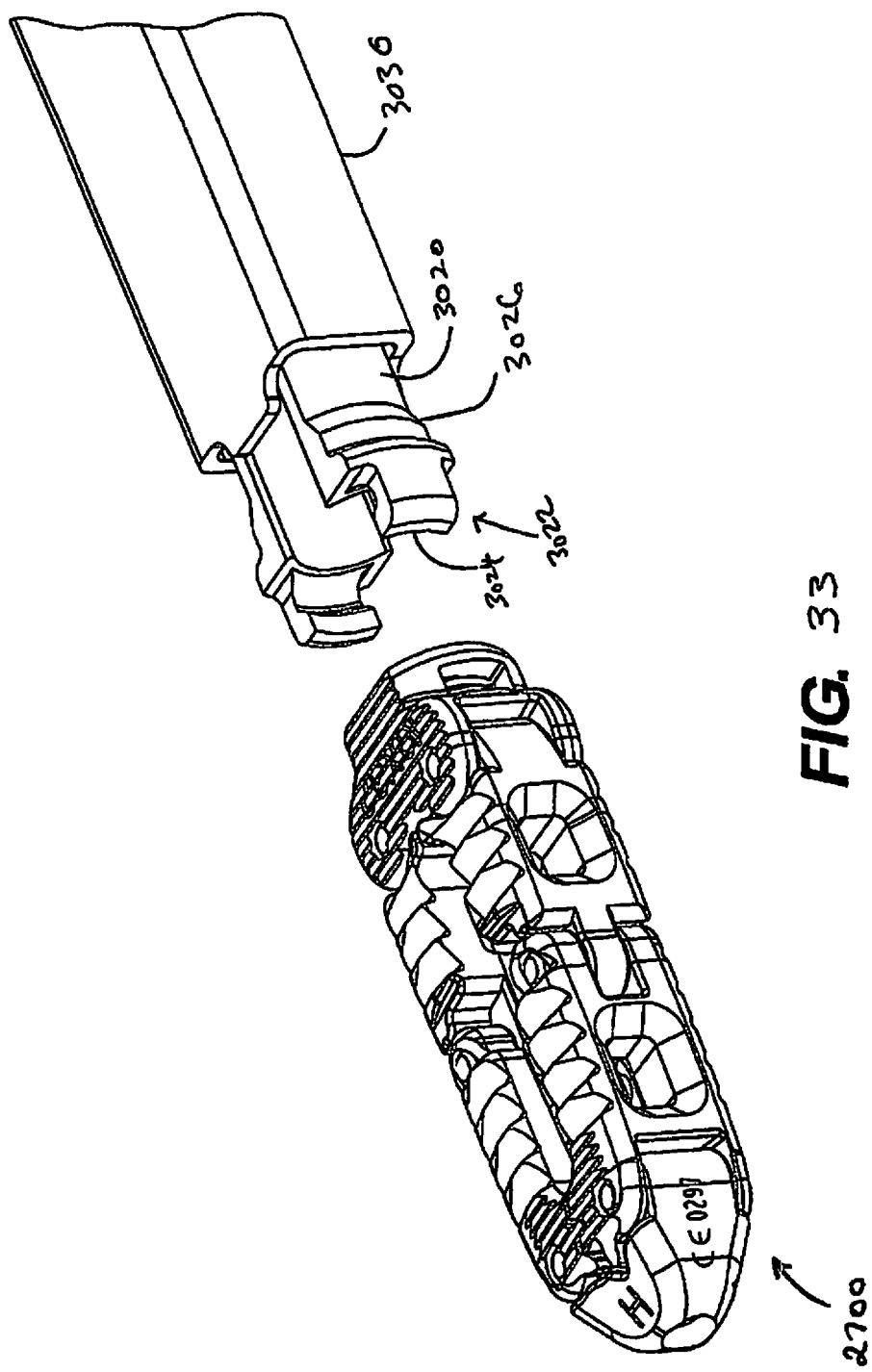

With reference to FIGS. 31 and 33, a distal portion of elongate structure 3012 may be configured in a fork-like configuration. More particularly, a distal portion of elongate structure 3012 may include a vertical slit 3016 defining two arms 3018 and 3020. Although only two arms 3018, 3020 are shown, those of ordinary skill in the art will understand that a greater or lesser number of arms may be contemplate in accordance with the principles of the present disclosure. For example, the distal portion of elongate structure 3012 may include only a single arm. Alternatively, elongate structure 3012 may include two longitudinal slits disposed in perpendicular planes, thereby creating four arms (not shown). As a result of one or more of the configuration of the elongate structure 3012, the configuration of slit 3016, and the material properties of elongate structure 3012, the arms 3018 and 3020 may exhibit resiliency or other spring-like characteristics. For examples, the arms 3018 and 3020 may be biased away from one another. In another embodiment, the arms 3018 and 3020 may be biased toward one another.

The arms 3018 and 3020 may be substantially similar to one another. Accordingly, for the purposes of efficiency, only the features of arm 3020 will be described. Those of ordinary skill will understand that arm 3018 may include one or more features of arm 3020. With specific reference to FIG. 33, a distal end 3022 of arm 3020 may be configured to releasably engage proximal portion 2702 of spacer 2700 via features 2706. More particularly, the distal end 3022 of arm 3020 may include a projection 3024 configured and shaped to be received within feature 2706. For example, as shown in FIG. 33, projections 3024 may be configured to extend towards each other. In some embodiments, feature 2706 may include a projection, and the distal end 3022 of arm 3020 may include a notch or other recess for releasably engaging the projection. Furthermore, a distal end portion of arm 3020 proximate to projections 3024 may include one or more geometric features configured for assisting in urging arm 3020 towards arm 3018 and vice versa. More particularly, an external surface of arm 3020 may include a rib 3026, which may be engaged by sleeve 3030 to urge arm 3020 toward arm 3018. The rib 3026 may include any suitable configuration known in the art. For example, in one embodiment, the rib may extend generally transverse to a longitudinal axis of the elongate structure 3012. In some embodiments, a proximal portion of rib 3026 may be configured to transition smoothly to an external surface of the remainder of arm 3020. That is, a proximal portion of rib 3026 may include a tapering or a generally ramp-like configuration. Further, although only one rib 3026 is depicted on arm 3020, those of ordinary skill will understand that any suitable number of ribs 3026 may be provided. Furthermore, the rib 3026 may include a height dimension that correlates to an amount of travel needed to move arm 3020 toward arm 3018 (and vice versa) so as to effectively engage spacer 2700.

With renewed reference to FIGS. 31 and 32A-B, a proximal end portion 3013 of elongate structure 3012 may be configured as follows. In one embodiment, the proximal end portion 3013 may include a horizontal slit 3028, which may extend from the proximal end of elongate structure 3012 distally to a position just proximal of knob 3032 on elongate structure 3012. The slit 3028 may define two arms 3028a, 3028b, which may be configured to be either biased away or toward one another. A proximal end of each arm 3028a, 3028b may be configured to assist securing the inserter fork to an actuator assembly, which will be discussed in greater detail below. In an embodiment, the proximal end of at least one of arms 3028a, 3028b may include a raised flange 3027.

As alluded to above, elongate structure 3012 may include a knob 3032 disposed thereon. Knob 3032 may include any suitable configuration. In one embodiment, knob 3032 may be disposed distally of slit 3028. An outer surface of knob 3032 may include suitable geometric features for securing knob 3032 within holder 3008. For example, an outer surface of knob 3032 may include a plurality of knurls, indents, recesses, and/or projections thereon. In one embodiment, knob 3032 may include a plurality of channels 3031 disposed thereon. The channels 3031 may be configured to receive at least one of ribs 3010 to facilitate securing knob 3032 with holder 3008. In some embodiments, elongate structure 3012 may include a mechanism for limiting longitudinal movement of elongate structure 3012 relative to holder 3008. For example, elongate structure 3012 may include a radially extending flange 3033 configured to abut one of arms 3009 or the base portion of U-shaped holder 3008 so as to prevent elongate structure 3012 from moving proximally relative to handle 3001. Furthermore, elongate structure 3012 may include a plurality of screw threads 3029 disposed on an external surface thereof. In one embodiment, the threads 3029 may be disposed proximally of slit 3016 but distally of flange 3033. As shown in FIG. 31, threads 3029 may be disposed substantially closer to flange 3033 than slit 3016.

Elongate structure 3012 may be configured to be received within a lumen 3030a of sleeve 3030. Sleeve 3030 may include any suitable configuration known in the art. For example, sleeve 3030 generally may include a configuration corresponding to an outer periphery of elongate structure 3012. More particularly, sleeve 3030 may include a distal portion having a substantially rectangular cross-sectional configuration, and a proximal portion having a substantially circular cross-sectional configuration. The lumen 3030a within sleeve 3030 may be similarly configured. That is, lumen 3030a may include a configuration that corresponds to an outer periphery of elongate structure 3012. That is, lumen 3030a may include a distal portion having a substantially rectangular cross-sectional configuration, and a proximal portion having a substantially circular cross-sectional configuration. A proximal portion of lumen 3030a may include a width dimension larger than a similar width dimension at a distal portion of lumen 3030a. In addition, a distal end of lumen 3030a may be configured to urge arms 3018 and 3020 towards one another so that they may engage spacer 2700, as discussed herein. Further, in one embodiment, sleeve 3030 may be a substantially elongate hollow member having a neck portion 3034 and a proximal lip 3036 at a proximal end thereof. Instead of lip 3036, those of ordinary skill in the art will understand that any suitable geometric configuration may be used within the principles of the present disclosure.

Prior to being received over elongate structure 3012, a proximal portion of sleeve 3030 may be operably coupled to an inserter knob 3038. Inserter knob 3038 may be any suitable knob known in the art and may include any suitable configuration. In one embodiment, knob 3038 may include a generally cylindrical configuration. However, any suitable configuration may be used in accordance with the principles of the present disclosure. Knob 3038 may include at least one lumen 3040. Lumen 3040 may extend completely through knob 3038 or partially therethrough. A distal portion of an inner surface of lumen 3040 may include at least one geometric feature 3042 for interacting with lip 3036 so as to retain inserter knob 3038 on sleeve 3030. In one embodiment, geometric feature 3042 may include a circumferential channel configured to receive lip 3036 therein. With reference now to FIG. 32A, lumen 3040 may include a plurality of screw threads 3044 for cooperating with threads 3029 on elongate structure 3012. Although the depicted embodiment illustrates that screw threads 3044 are disposed at a proximal portion of lumen 3040, threads 3044 may be disposed along any portion of lumen 3040. For example, in one embodiment, threads 3044 may extend from a midpoint of lumen 3040 to a proximal end thereof.

With reference now to FIGS. 31-32C, actuator assembly 3050 will be described. Actuator assembly 3050 may include a plurality of components operably coupled together and operable to facilitate expanding spacer 2700, as discussed below in greater detail. Although the plurality of components are described individually, those of ordinary skill in the art will appreciate that any of the described components may be combined with one or more of the other components and/or eliminated altogether without departing from the principles of the present disclosure.

Actuator assembly 3050 may include a central portion 3052, which may include a proximal head 3054 and an elongate tubular member 3056 extending therefrom. Central portion 3052 may define a lumen 3058. Lumen 3058 may extend completely through central portion 3052. Lumen 3058 may include any suitable configuration known in the art. For example, as shown, lumen 3058 may include a substantially circular cross-sectional configuration. In one embodiment, proximal end 3054 may include a channel 3060 for receiving a locking tab 3062 therein, which will be discussed in greater detail below. Channel 3060 may include any suitable configuration, and may be dimensioned and shaped to correspond to locking tab 3062. Further, channel 3060 may be configured to cut through lumen 3058, as shown in FIG. 32B. In addition, a portion of lumen 3058 may include a plurality of screw threads 3064. The screw threads 3064 may be disposed along any portion of lumen 3058. For example, in the depicted embodiment, screw threads 3064 may be disposed along only a proximal portion of lumen 3058. Screw threads 3064 may be disposed in lumen 3058 on either side of channel 3060. The screw threads 3064 may extend until a proximalmost end of lumen 3058.

Externally, proximal head 3054 may include any suitable configuration. In the depicted embodiment, for example, proximal head 3054 may include a substantially planar proximal end face 3066. The end face 3066 may include an opening 3067 in communication with lumen 3058. In addition, end face 3066 may include a second opening 3068 for receiving a retention pin 3069 therein. Opening 3068 include a diameter that is smaller than opening 3067. As will be discussed below, retention pin 3067 may be disposed in opening 3068 for retaining tab 3062 in channel 3060. Proximal head 3054 may include a generally circular cross-sectional configuration. In one embodiment, however, proximal head 3054 may include substantially planar superior 3070 and inferior (not shown) surfaces. As depicted in FIG. 32C, planar superior surface 3070 may include an opening 3071 in communication with channel 3060 for receiving tab 3062 therein. With continued reference to FIGS. 32B-32C, central portion 3052 may include any suitable external configuration known in the art. In one embodiment, central portion 3052 may include a substantially uniform external configuration. In the depicted embodiment, central portion 3052 may include a step 3072. Step 3072 may be located at any portion along a length of central portion 3052. In one embodiment, step 3072 may be located at a midpoint of central portion 3052. Step 3052 may include any suitable configuration. For example, step 3052 may be the interface between a relatively smaller diameter distal portion 3052a of central portion 3052 and a relatively larger diameter proximal portion 3052b of central portion 3052. As shown in, e.g., FIG. 32C, step 3072 may include a ramped surface in some embodiments. Further, a portion of proximal portion 3052b may be configured to receive sleeve member 3076 thereon. Accordingly, proximal portion 3052b may include one or more suitable geometric configurations, such as, e.g., screw threads 3074, for coopering with corresponding screw threads 3077 within sleeve member 3076, as described in greater detail below. Screw threads 3074 may extend along any portion of proximal portion 3052b. For example, screw threads 3074 may extend along a substantial entirety of proximal portion 3052b or only for a portion thereof.

Distal portion 3052 may be configured, sized, and dimensioned to be received within a lumen defined by arms 3028a and 3028b. In one embodiment, distal portion 3052 may include a diameter (or if not tubular, a width dimension) that is larger than a diameter (or width dimension) of the lumen defined by arms 3028a, 3028b, so as to spread apart arms 3028a, 3028b when distal portion 3052 is received therebetween. In this manner, distal portion 3052 may be frictionally retained by the inherent resilient properties of arms 3028a, 3028b acting on distal portion 3052. To facilitate with orientation and guiding distal portion 3052 into the lumen defined by arms 3028a, 3028b, distal portion 3052 may include one or more projections 3075, which may be configured to be slidably received within slit 3028.

As noted above, opening 3071 and channel 3060 may be configured to receive therein a locking tab 3062 for receiving a tool within lumen 3058 of actuator 3050. Tab 3062 may include any suitable configuration known in the art. In one embodiment, tab 3062 may be resiliently biased in a direction out of channel 3060 by one or more springs or spring like members 3063. Further, tab 3062 may be retained in channel 3060 by retention pin 3069, described above. Tab 3062 may further define a passageway 3062a therethrough. Passageway 3062a may include any configuration known in the art. As discussed below, passageway 3062a may be configured (e.g., may include one more projections) to engage channel 3206 of threaded shaft 3200 for retaining threaded shaft within actuator assembly 3050.

Sleeve 3076 may include a generally cylindrical member defining a lumen 3078 therethrough. Sleeve 3076 may include any suitable configuration known in the art. In one embodiment, sleeve 3076 may include a generally circular cross-sectional configuration. However, sleeve 3076 may include any suitable cross-sectional configuration. Further, a distal end of sleeve 3076 may include a generally tapered configuration. Lumen 3078 may include a generally circular cross-sectional configuration, and may be configured to receive proximal portion 3052b therein. Indeed, as alluded to above, lumen 3078 may include a plurality of threads 3077 configured to mate with threads 3074 to retain sleeve 3076 on central portion 3052. Threads 3077 may extend along any suitable portion of lumen 3078. In one embodiment, for example, threads may extend an entirety of lumen 3078. In another embodiment, threads 3077 may extend along only a portion of lumen 3078.

An overall maximum diameter of sleeve 3076 may be less than a diameter or width of proximal head 3054. In addition, sleeve 3076 may include a step 3079 that defines an interface between a relatively larger diameter distal portion 3076b of sleeve 3076 and relatively smaller diameter proximal portion 3076a of sleeve 3076. Step 3079 may be disposed at any suitable location along sleeve 3076. Further, sleeve 3076 may include one or more longitudinal grooves 3080 extending distally from a proximal end thereof. The grooves 3080 may be configured to receive rods 3081 therein, which may be configured to prevent sleeve 3076 from rotating within housing 3090 of actuator 3050, as described below in greater detail.

Figure 32B:
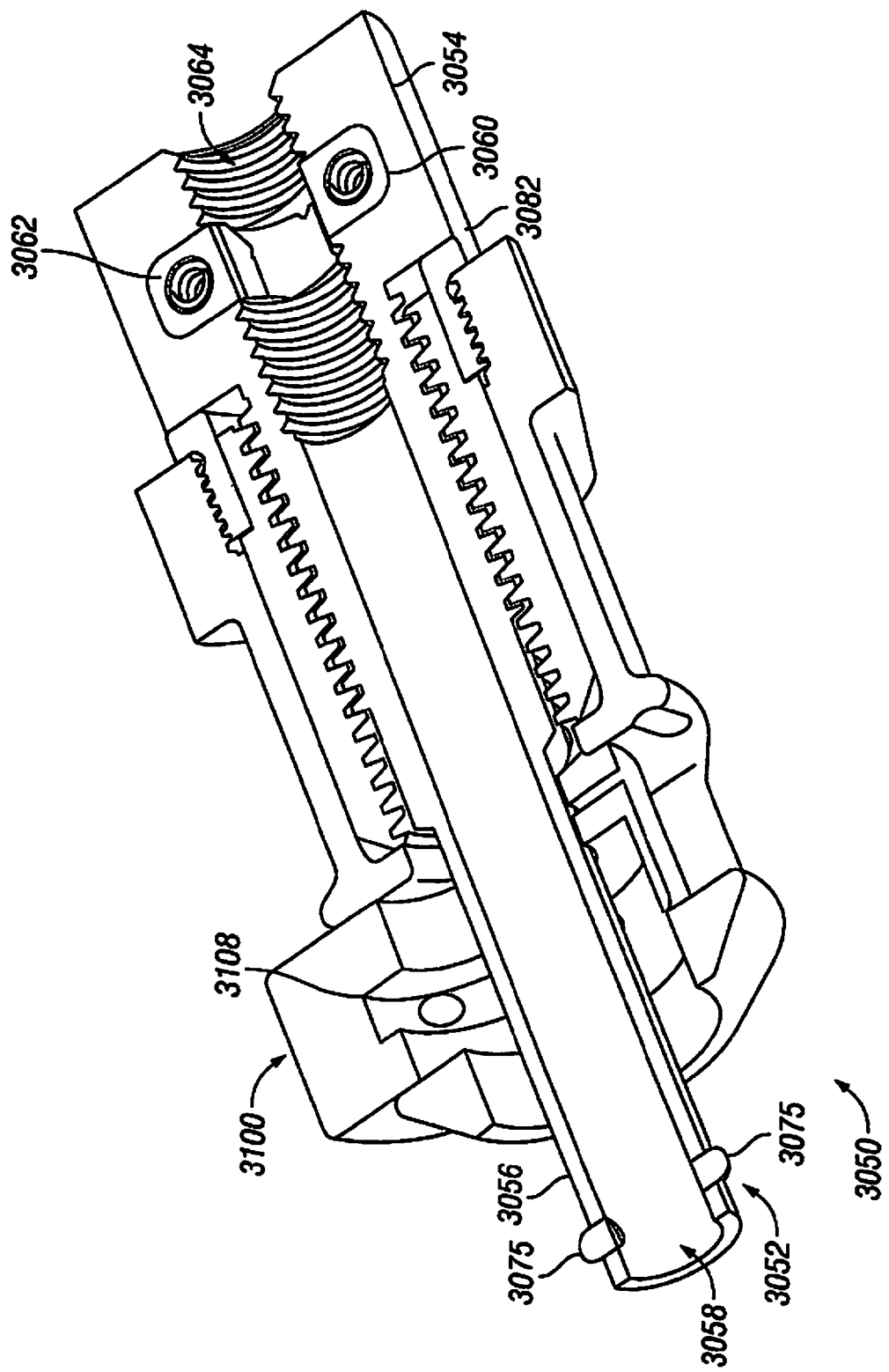
FIG. 32B depicts a cross-sectional view of an actuator assembly.

A washer 3082 may be configured to be frictionally retained on proximal portion 3076a, as shown in FIG. 32B. Washer 3082 may include a generally cylindrical structure that defines a lumen 3084 therethrough. In addition, washer 3082 may define a proximal ledge 3085 configured to abut a distal face of proximal head 3054. Washer 3082 may also include a plurality of external threads 3086 for securing housing 3090 thereon.

Housing 3090 may include a generally cylindrical structure defining a lumen 3092 therethrough. Lumen 3092 may include any suitable configuration known in the art. For example, lumen 3092 may include a generally circular cross-sectional configuration. However, any suitable cross-sectional configuration may used within the principles of the present disclosure. In embodiments where lumen 3092 includes a circular cross-sectional configuration, lumen 3092 may include a generally constant diameter throughout its length or a diameter that varies over the length of lumen 3092. For example, a proximal portion of lumen 3092 may include a counter bore and therefore may include a larger diameter than a remainder of lumen 3092. A proximal portion of lumen 3092 may also include screw threads 3093 for threadingly engaging threads 3086 of washer 3082 to retain housing 3090 thereon. Threads 3093 may extend along any suitable portion of lumen 3092. Walls of lumen 3092 may include one or more grooves 3094, which may correspond to grooves 3080 and be configured to receive rods 3081. Rods 3081, grooves 3904, and grooves 3080 cooperate to prevent sleeve 3076 from rotating within housing 3090. Further, housing 3090 may be made of any suitable biocompatible material known in the art, including, for example, PEEK.

Externally, housing 3090 may include any suitable configuration known in the art. In the depicted embodiment, housing 3090 may include a raised proximal portion 3095. Proximal portion 3095 may include any suitable configuration. In one embodiment, proximal portion 3095 may include a hexagonal configuration (e.g., a hexagonal cross-sectional configuration) for being engaged by an appropriately configured tool. Similarly, proximal portion 3095 may include one or more geometric features 3096 configured to assist with retaining a tool (discussed below) on proximal portion 3095. The geometric features 3096 may include a plurality of indentations, bumps, recesses, channels, etc. Housing 3090 may further include a raised distal portion 3097. Raised distal portion 3097 may define a channel 3098 through housing 3090. Channel 3098 may include any suitable configuration. For example, in one embodiment, channel 3098 may extend in a direction that is substantially perpendicular to a longitudinal axis of lumen 3092. Channel 3098 may be configured to receive catch 3100 slidably therein. Further, raised distal portion 3097 may include one or more openings 3099 for receiving fasteners 3099a therein. In embodiments where fasteners 3099 include threaded fasteners such as, e.g., screws, openings 3099 may include corresponding threads.

Catch 3100 may include any suitable configuration, and may be dimensioned and shaped to be received within channel 3098. Catch 3100 may be made of any suitable material known in the art, including, e.g., PEEK. In one embodiment, catch 3100 may include a substantially rectangular configuration. As shown in FIG. 31C, lateral surfaces 3102 of catch 3100 may be radiused or curved so that an outer profile of catch 3100 may correspond to raised distal portion 3097 when catch 3100 is received within channel 3098. Further, superior 3104 and/or inferior surfaces of catch 3100 may include one or more openings corresponding to openings 3099. As shown in FIG. 32C, opening 3104 may include any suitable configuration. For example, opening 3104 may include a substantially elongate configuration, whereby fastener 3099a may be slidably disposed in opening 3104. Consequently, catch 3100 may be configured to slide back and forth relative to channel 3098 without becoming disengaged when fasteners 3099 are disposed in openings 3104. Moreover, catch 3100 may define a passageway 3106 therethrough for receiving flange 3027 (at the proximal end of the inserter fork shown in FIG. 31) and/or distal portion 3052a therethrough. Passageway 3106 may include any suitable configuration known in the art. In one embodiment, a wall of passageway 3106 may define a circumferential channel 3108 (shown in FIG. 32B) configured to engage flange 3027. The circumferential channel 3108 may be disposed completely around passageway 3106 or only partially around passageway 3106.

Figure 34:
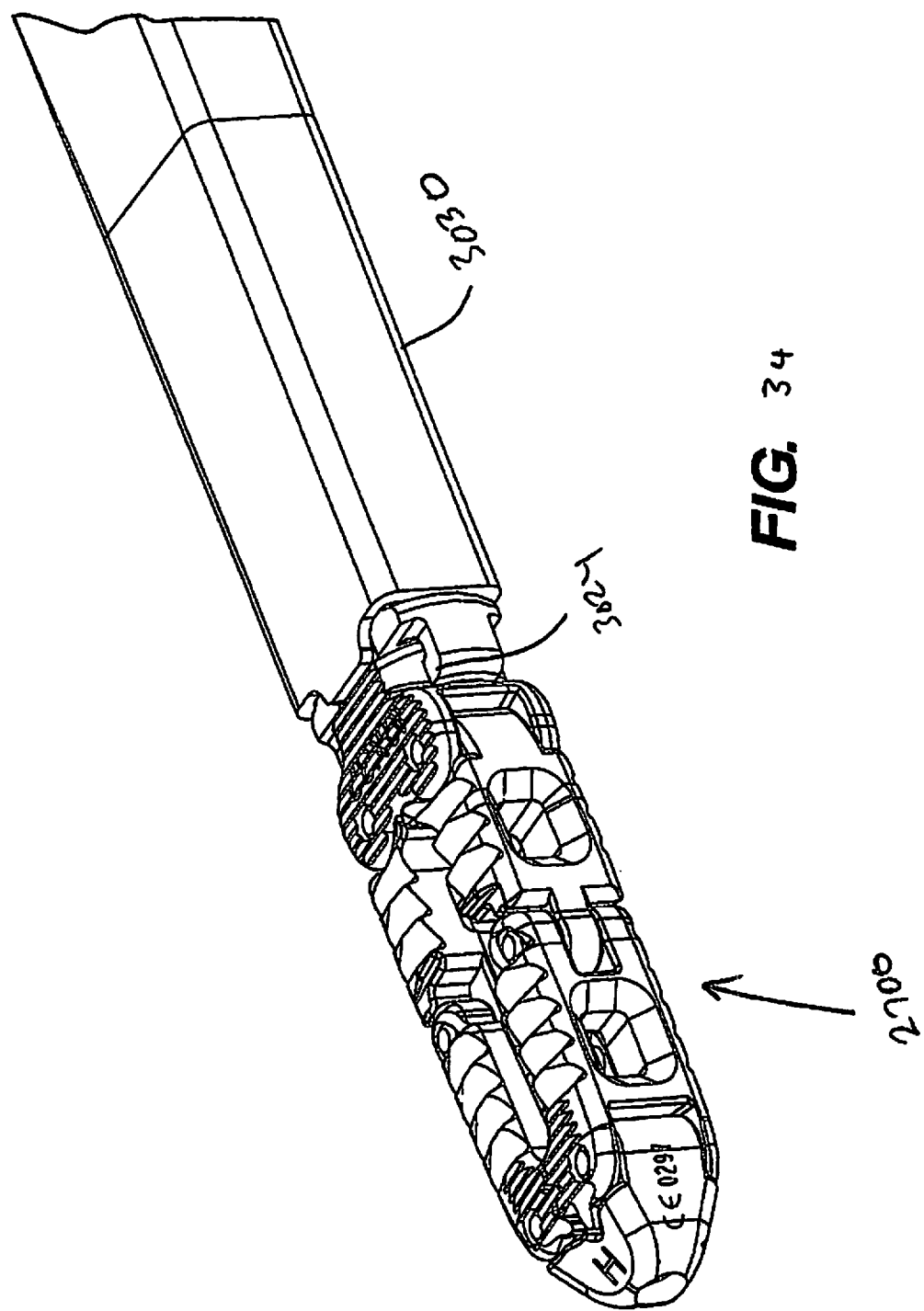

With reference now to FIGS. 34-44 a method of operating tool 3000 and its various components to implant an exemplary embodiment of spacer 2700 will be described. As shown in FIG. 34, sleeve 3030 may be advanced distally to squeeze arms 3018, 3020 towards one another so that projections 3024 may engage features 2706 to secure spacer 2700 to tool 3000. Sleeve 3030 may be moved distally by rotating knob 3038 relative to elongate structure 3012. As a result of the coupling via threads 3044 and 3029, rotating knob 3038 relative to elongate structure 3012 may result in knob 3038 and sleeve 3030 moving longitudinally relative to elongate structure 3012.

Once the spacer 2700 is secured to tool 3000, the spacer 2700 may be ready for implantation within a patient. As discussed above, spacer 2700 may be delivered to the interbody disc space within a patient via any suitable procedure known in the art. For example, in one embodiment, the spacer is delivered via an anterior approach. In another embodiment, the spacer may be delivered via a posterior approach. Further, the approach angle may be any suitable angle known in the art. For example, the spacer 2700 may be delivered by tool 3000 inserted via a posterior approach at an angle of 20-40 degrees offset from a center line of a patient.

Figure 35:
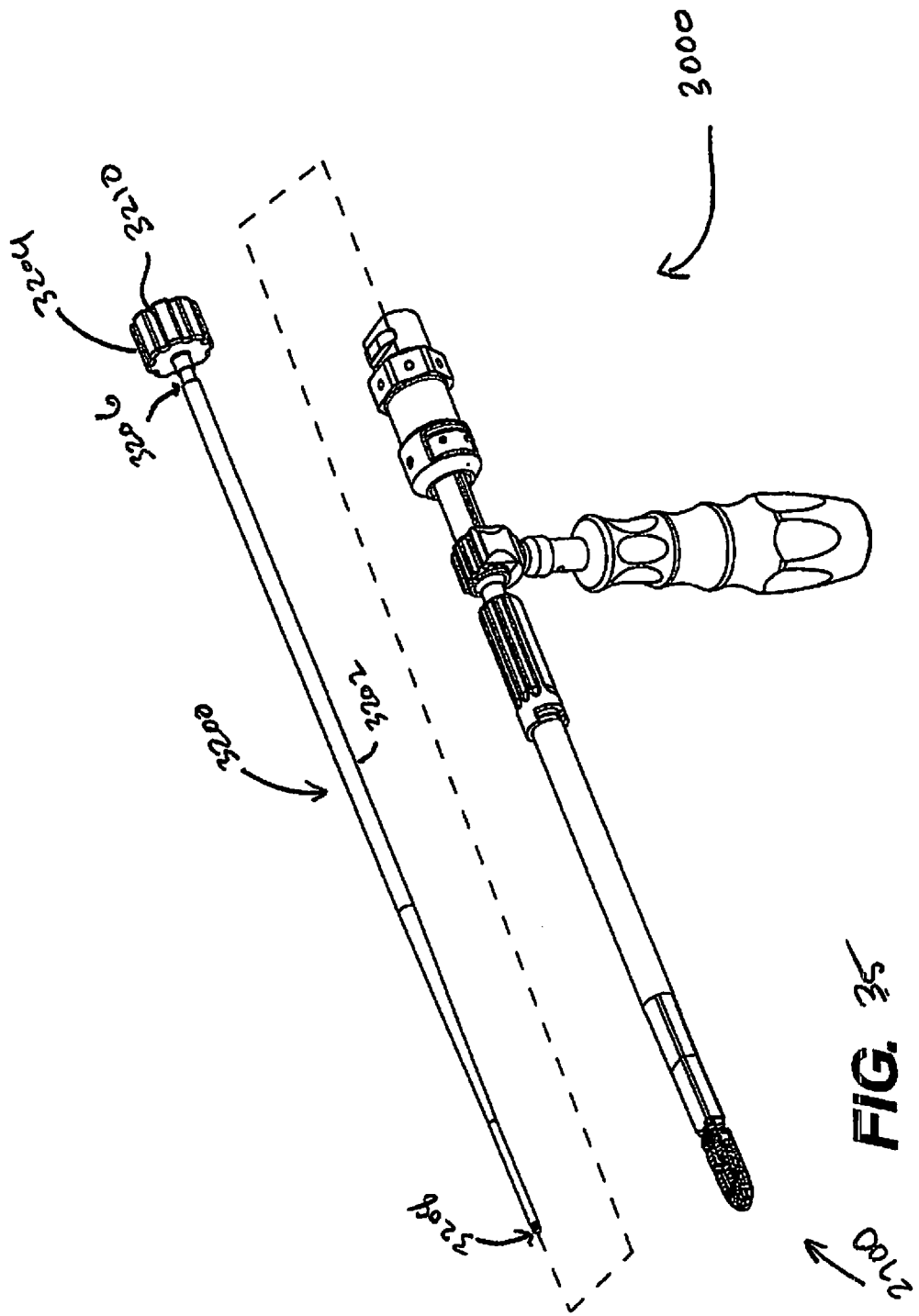

Once spacer 2700 is secured to the distal end of the inserter fork, a threaded shaft 3200 may be inserted into a proximal end of actuator assembly 3050 and all the way through the distal end of sleeve 3030 into lumen 2705 of proximal portion 2702 and threaded into lumen 2744 of distal component 2740 of spacer 2700. With reference to FIG. 35, threaded shaft 3200 may include any suitable configuration. In one embodiment, threaded shaft 3200 may include an elongate member 3202. Elongate member 3202 may include any suitable configuration. In embodiment, elongate member 3202 may include a generally cylindrical configuration. For example, elongate member 3202 may include a generally circular cross-sectional configuration. Further, elongate member 3202 may be configured to gradually taper toward its distal end. That is, a proximal portion of elongate member 3202 may include a diameter that is relative larger than a distal portion of elongate member 3202.

In one embodiment, a distal portion, e.g., a distal end, of elongate member 3202 may be configured to engage distal component 2740 of spacer 2700. For example, a distal portion of elongate member 3202 may include one or more geometric configurations configured to cooperate with geometric configurations disposed within lumen 2744 of distal component 2740. In embodiments where lumen 2744 may include threads, for example, a distal portion of elongate member 3202 may also include threads 3208.

A proximal end of elongate member 3202 may include an actuating member 3204. Actuating member 3204 may include any suitable configuration known in the art. In one embodiment, actuating member 3204 may be removably coupled to a proximal portion of elongate member 3202. In another embodiment, actuating member 3204 may be integrally formed with elongate member 3202. Actuating member 3204 may include a knob or a handle in some embodiments. Accordingly, actuating member 3204 may include one or more geometric configurations 3210 to facilitate gripping by an operator. Geometric configurations 3210 may include ridges, channels, protrusions, projections, dents, bumps, recesses, surface texturing, etc. Further, elongate member 3202 may include a channel 3206. Channel 3206 may be disposed at any suitable position along elongate member 3202. In one embodiment, channel 3206 may be disposed closer to a proximal end of elongate member 3202 than a distal end. Channel 3206 may be defined by a portion of elongate member 3202 including a relatively smaller diameter than immediately adjacent portions of elongate member 3202. Channel 3206 may be positioned at a location on elongate member 3202 suitable for being engaged by passageway 3062*a* (shown in FIG. 32C). Further, actuating member 3204 may include one or more markings 3212 (shown in FIG. 38A) for indicating a degree of expansion of spacer 2700, as described further below. The markings 3212 may include any suitable markings known in the art and may include numerical values corresponding to a percentage of expansion of spacer 2700.

Figure 36:
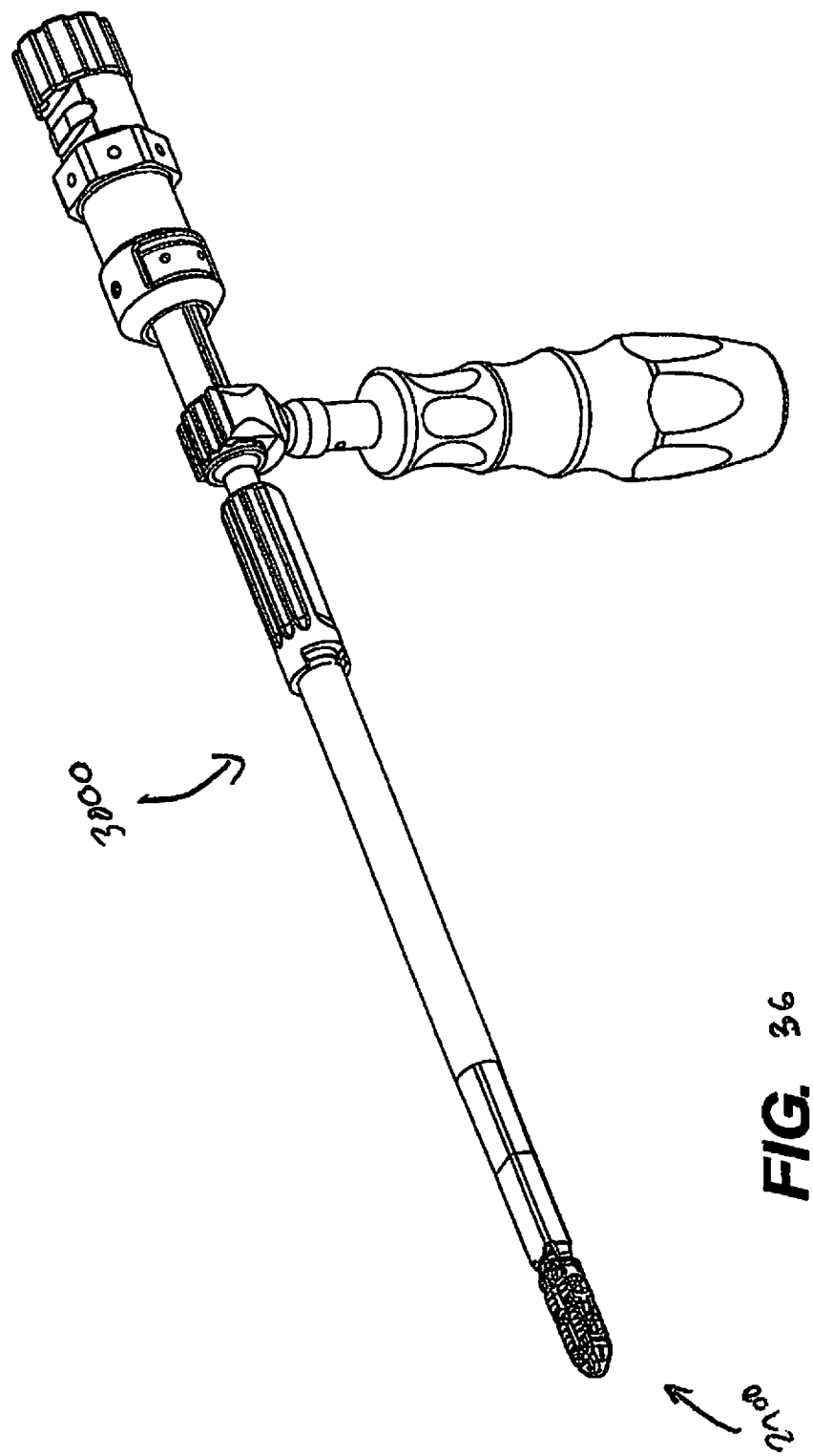

Turning now to FIG. 36, tool 3000 may be secured to spacer 2700 and threaded shaft 3200 may be received within tool 3000. Tool 3000 may be then inserted into a patient to effect implantation of spacer 2700 within the patient. In some embodiments, however, tool 3000 and spacer 2700 may be already positioned within a patient when threaded shaft 3200 is inserted into tool 3000 and secured to spacer 2700.

Figure 37:
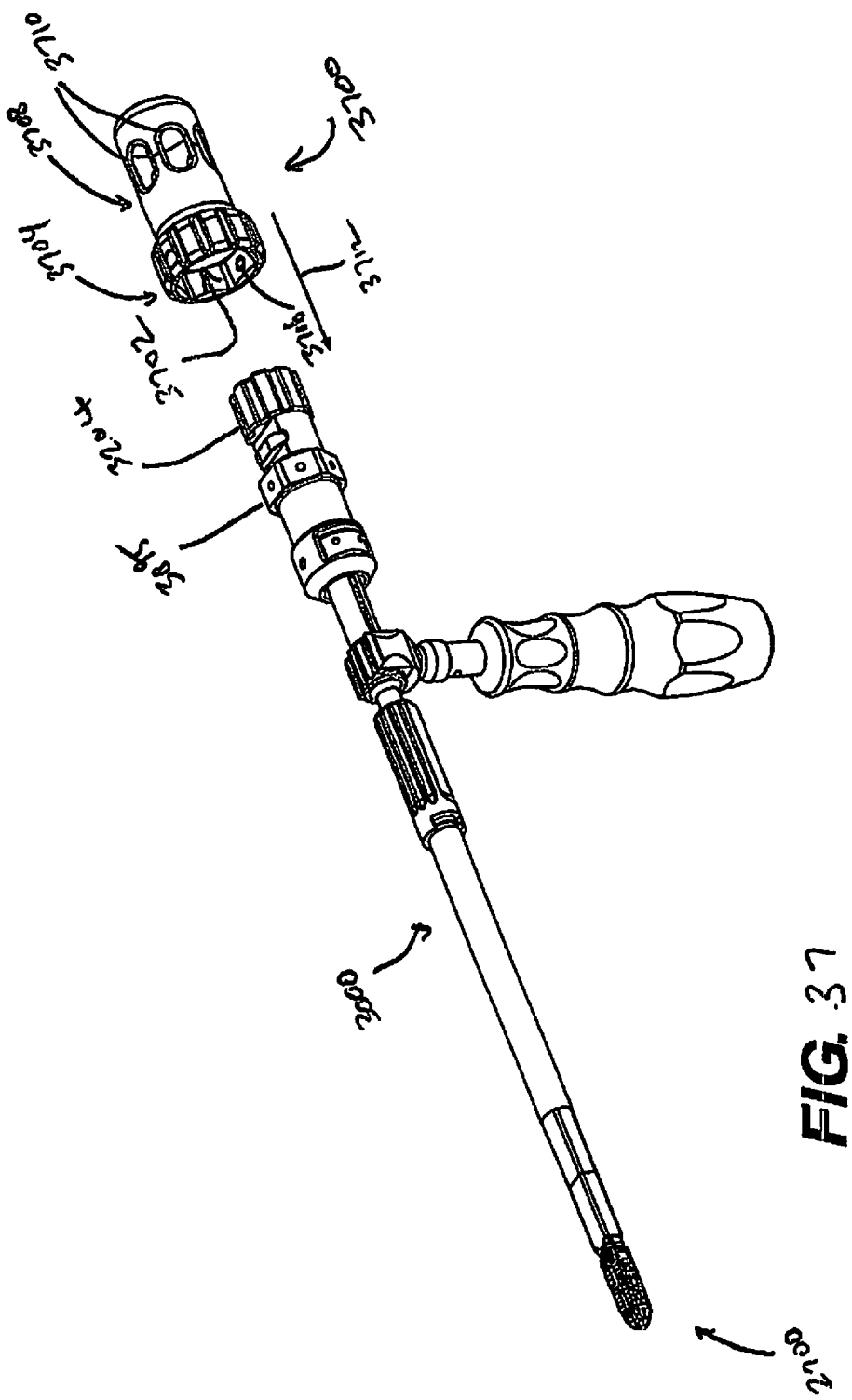
Figure 38:
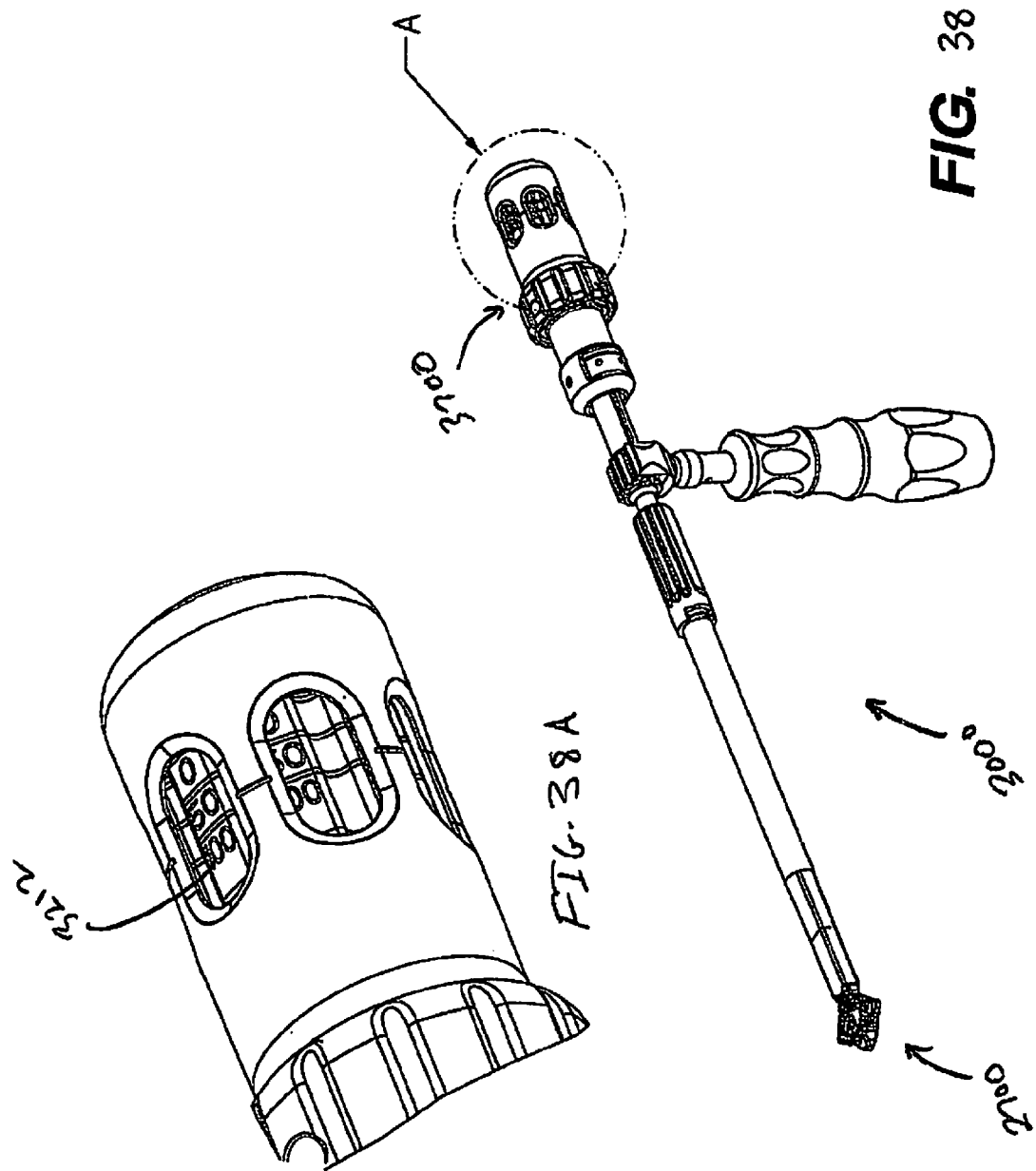
Figure 39:
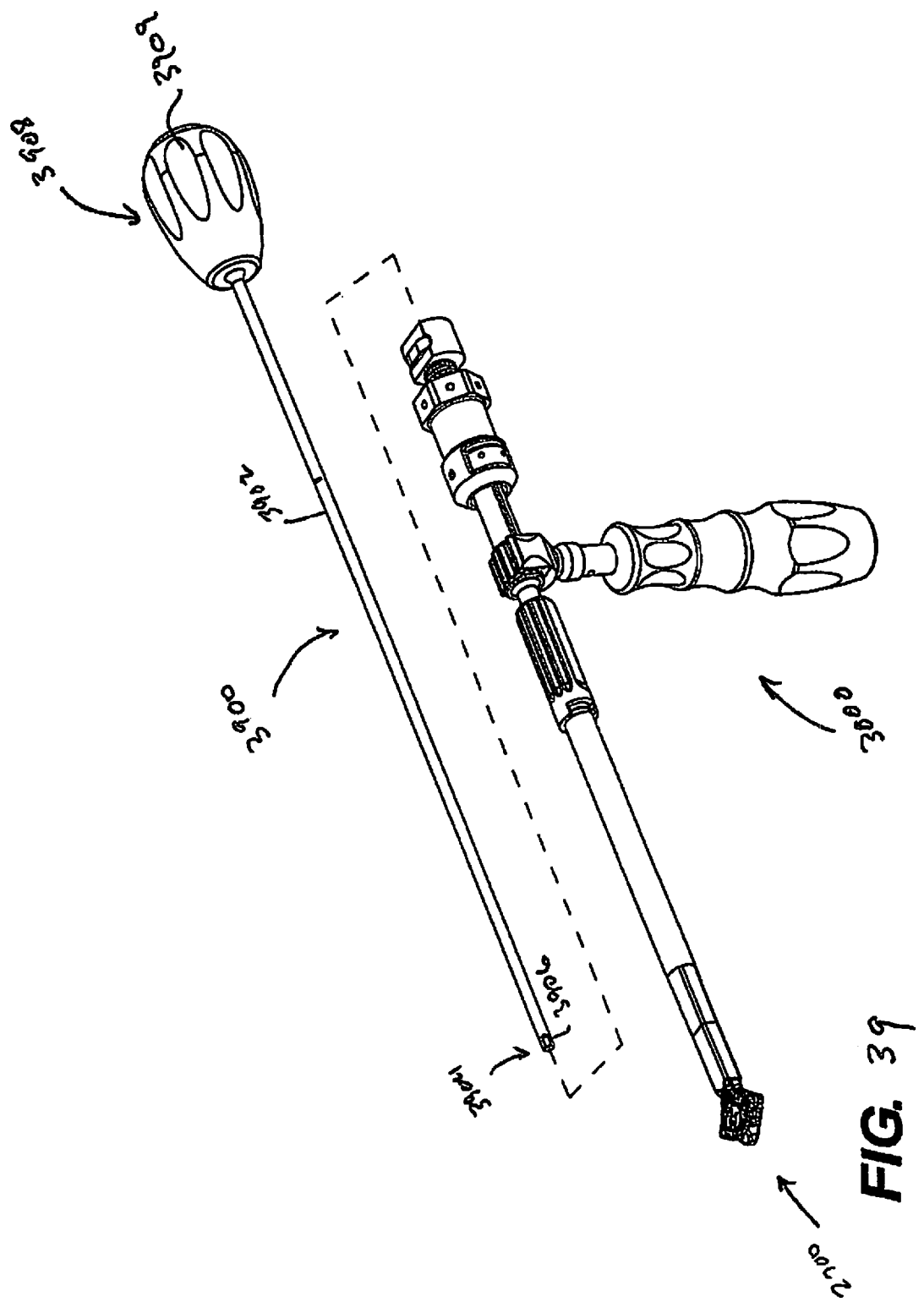
Figure 46:
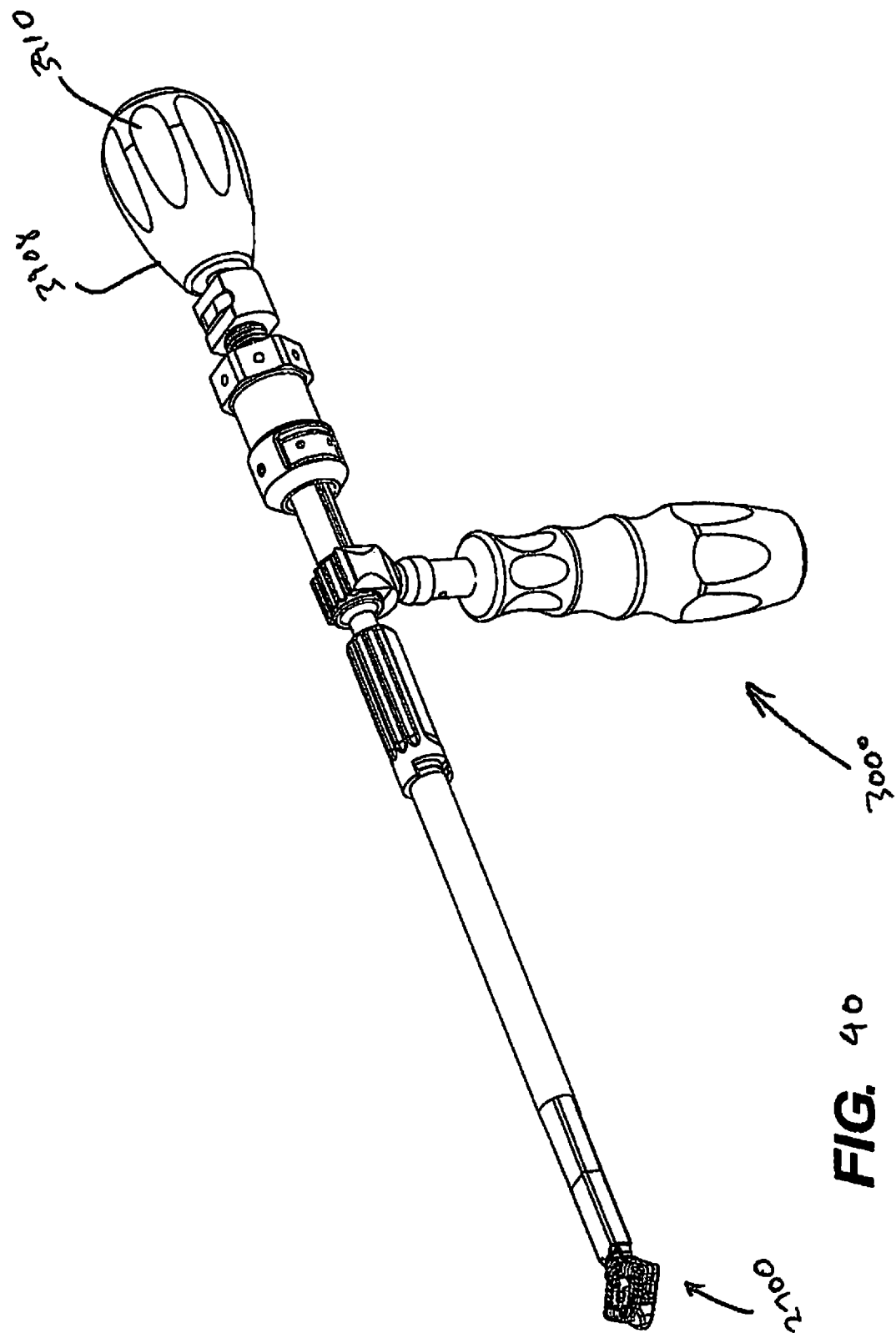

Turning now to FIG. 37, an expanding hex cap 3700 may be positioned over a proximal end of tool 3000 and actuating member 3204. In one embodiment, hex cap 3700 may include a generally cylindrical member defining a lumen 3702 therein. Lumen 3702 may extend completely through hex cap 3700 or may be blind, such that hex cap 3700 includes a closed proximal end. A distal end portion 3704 of hex cap 3700 may be configured to be received over and engage proximal portion 3095. Accordingly, distal end portion 3704 may include a configuration that corresponds to proximal portion 3095. For example, distal end portion 3704 may be shaped as a hexagonal tool. Further, an inner surface of lumen 3702 in distal portion 3704 may include one or more geometric features 3706 configured to engage geometric features 3096 on proximal portion 3095. In one embodiment, geometric features 3706 may include a plurality of bumps while geometric features 3096 may include a plurality of recesses, or vice versa. In addition, as depicted in FIG. 37, distal end portion 3704 may include a diameter relatively larger than a proximal portion 3708 of hex cap 3700

Further, a proximal portion 3708 of hex cap 3700 may include a plurality of windows or openings 3710 disposed radially thereabout. The openings 3710 may include any suitable configuration known in the art and may facilitate visualizing the markings 3212 disposed on actuating member 3204. Proximal portion 3708 may include any suitable number of openings desired.

In operation, and while spacer 2700 is appropriately positioned (e.g., by moving hex cap 3700 in the direction of arrow 3712) within a patient, hex cap 3700 may be positioned over a proximal end of tool 3000 so that distal end portion 3704 may engage proximal portion 3095 of actuator assembly and actuating member 3204 may be visible to an operator through openings 3710. Next, the operator may rotate hex cap 3700 to expand spacer 2700 until the desired amount of expansion if achieved. Rotating hex cap 3700 causes proximal portion 3095 (and, consequently, housing 3090) to be rotated via its engagement with distal end portion 3704. As a result of the various components and their connections of actuator assembly 3050 described above, when housing 3090 is rotating, sleeve 3076 is also rotated because it is fixed relative to housing 3090 via rods 3081. Consequently, sleeve 3076 and housing 3090 are translated longitudinally relative to central portion 3052. Further, because a proximal end flange 3027 is secured to housing 3090 via catch 3100, the entire inserter fork also translates longitudinally relative to central portion 3052 when hex cap 3700 is rotated. And, since threaded shaft 3200 is secured to central portion 3052 via catch 3206 and tab 3062, the distal threads 3208 threaded into distal component of spacer 2700 may move relative to proximal portion 2702 of spacer 2700 as the inserter fork is moved when hex cap 3700 is rotated. Such relative movement between the distal end of the inserter fork and the threaded shaft 3200 causes proximal portion 2702 to move towards distal component 2740, thereby effecting expansion of spacer 2700 as the various components of spacer are rotated from the positions depicted in FIG. 27B to the positions depicted in FIG. 27A or any suitable, desired intermediate position. As alluded to above, a degree of travel of, e.g., housing 3090 relative to actuating member 3054 may correspond to a degree of expansion of spacer 2700. Accordingly, actuating member 3054 may include a plurality of markings to assist an operator in determining a degree of expansion of spacer 2700.

After desired expansion of spacer 2700 is achieved and spacer 2700 is appropriated positioned within the patient, hex cap 3700 may be removed. Subsequently, tab 3062 may be actuated (e.g., depressed) so that it may temporarily be disengaged from channel 3206 and threaded shaft 3200 may be also removed from tool 3000. In the meantime, position retaining features 2721 and 2727 may interfere with one another to frictionally retain an expanded configuration of spacer 2700. Subsequently, a locking instrument 3900 may be inserted into lumen 3058 and advanced through tool 3000 until it engages within locking feature 2760.

Locking instrument 3900 (see FIG. 39) may include a generally elongate member 3902 having a distal portion 3904 including one or more geometric configurations 3906 configured to engage with geometric configurations 2762*a* in such a manner that when locking instrument 3900 is rotated, locking feature 2760 will be rotated. As its proximal end, locking instrument may include a suitable actuating member, such as, e.g., a handle or knob 3908. Handle or knob 3908 may be secured to elongate member 3902 by any suitable means known in the art. In one embodiment, handle or knob 3908 may be removably coupled to elongate member 3902. In other embodiments, handle or knob 3908 may be integrally formed with elongate member 3902. In some embodiments, locking instrument 3900 may be a torque limiting tool. That is, locking instrument 3900 may be configured to prevent application of torque above a predetermined limit. For example, once a predetermined limit of applied torque is exceeded, handle or knob 3908 may rotate freely relative to elongate member 3902. Handle or knob 3908 may include any suitable configuration known in the art to facilitate gripping and operation by a user. In one embodiment, handle or knob 3908 may include one or more geometric features 3909 (e.g., detents, recesses, protrusions, etc.) configured to allow manipulation by a user.

In operation, distal portion 3904 may be inserted into lumen 2762 so as to engage geometric configurations 2762*a*, as shown in FIG. 40. Next, handle or knob 3908 may be rotated to advance locking feature 2760 into space 2708 to prevent links 2710 from returning to their collapsed position, thereby locking spacer 2700 in the expanded configuration.

Next, locking instrument 3900 may be removed from tool 3000 and a funnel tube 4100 (see FIG. 41) having a funnel 4200 removably coupled thereto may be inserted into tool 3000 via lumen 3058. Funnel tube 4100 may include any suitable configuration known in the art. In one embodiment, funnel tube 4100 may include an elongate member 4102 defining a lumen 4104 therethrough. Elongate member 4102 may include any suitable configuration. For example, elongate member 4102 may include a generally circular cross-sectional configuration. In some embodiments, however, other cross-sectional configurations, such as, e.g., rectangular, may be used. Similarly, lumen 4104 may include a substantially circular cross-sectional configuration, but any suitable configuration may be employed within the principles of the present disclosure. Elongate member 4102 may have a length sufficient to extend from outside a proximal-most end of tool 3000 to beyond a distal end of locking feature 2760, so as to deliver material into a center of spacer 2700 when it is in the expanded configuration, as discussed below in greater detail.

A proximal end portion 4106 of elongate member 4102 may be configured to be removably secured within lumen 3058. More particularly, proximal end portion 4106 may include threads 4108 configured to engage threads 3064 in proximal head 3054 so as to retain funnel tube 4100 therein. Funnel tube 4100 may further include a knob 4110 disposed proximally of threads 4108. In some embodiments, knob 4110 may include a diameter that is relatively larger than a diameter of a remainder of funnel tube 4100. In addition, knob 4110 may define a lumen (not shown) therethrough. In some embodiments, the lumen of knob 4110 may include a diameter that is relatively larger than a diameter of the lumen 4104 through a remainder of funnel tube 4100. Knob 4110 may also include a plurality of geometric configurations 4112 located on an external surface thereof. The geometric configurations 4112 may include any suitable configuration known in the art. In one embodiment, the geometric configurations may include a plurality of raised ridges, bumps, notches, recesses, detents, etc.

Funnel 4200 may be any suitable funnel known in the art. For example, funnel 4200 may include a conical portion 4202 having a tapering cavity therein. The conical portion 4202 may be secured to or integrally formed with a neck portion 4204 having a lumen defined therethrough. The lumen in neck portion 4204 may be in communication with conical portion 4202. Neck portion 4204 may be removably secured to proximal end portion 4106 by any suitable means known in the art. In one example, neck portion 4204 may include threads configured to matingly engage corresponding threads 4113 (shown in FIG. 43) disposed on proximal end portion 4106. In one embodiment, a portion of proximal end portion may be received within neck portion 4204. In another embodiment, a portion of neck portion 4204 may be received within proximal end portion 4106.

Figure 42:
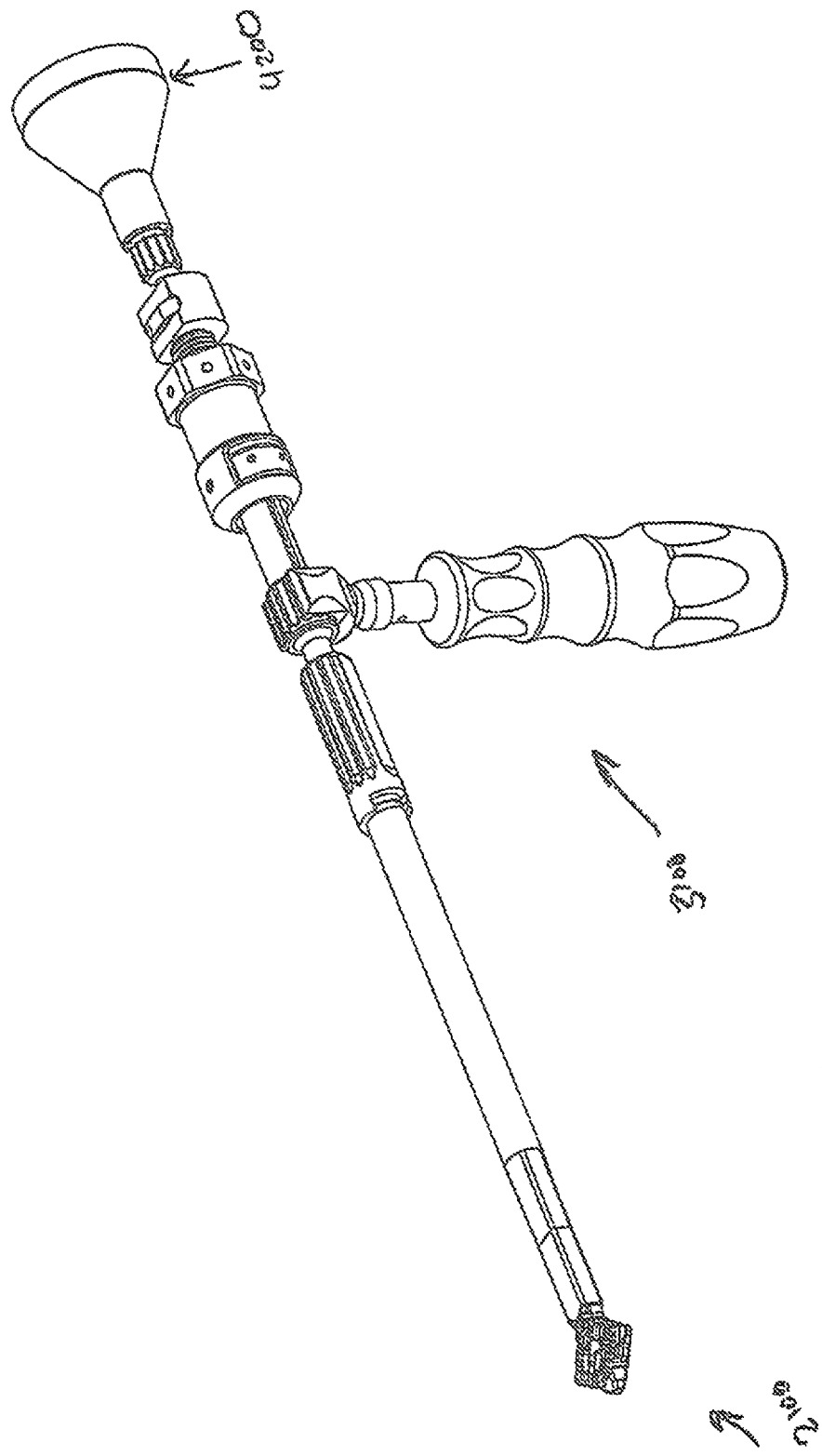

In use, funnel tube 4100 may be advanced into lumen 3058 and secured therein by engaging threads 4108 with threads 3064, such that a distal opening of lumen 4104 is disposed through locking feature 2760 within spacer 2700, as shown in FIG. 42. Next, the space within spacer 2700 may be filled with morcellated bone (e.g., autograft) or any other suitable material into the center of spacer 2700 when it is in the expanded position. Subsequently, funnel 4200 may be decoupled from funnel tube 4100 by, e.g., unscrewing it. Next, a bone funnel pusher 4300 may be inserted through funnel tube 4100 to push or advance any morcellated bone graft or other material remaining in funnel tube 4100 out of funnel tube 4100 and into a center of spacer 2700.

Figure 43:
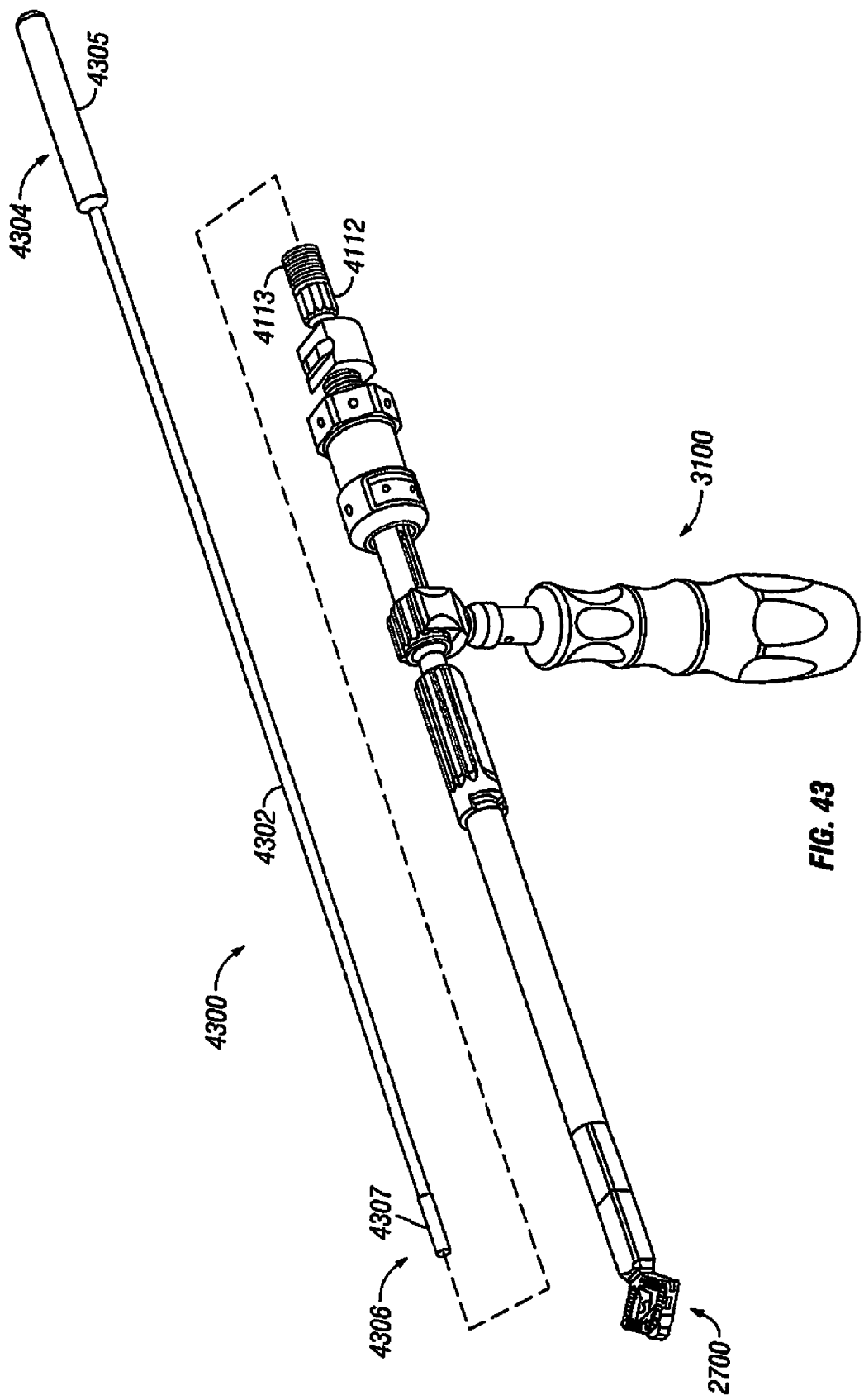

As shown in FIG. 43, bone funnel pusher 4300 may include a generally elongate member 4302 having a proximal end 4304 and a distal end 4306. Pusher 4300 may include any suitable configuration known in the art. Elongate member 4302 may include any suitable configuration known in the art. For example, elongate member 4302 may include a generally circular cross-sectional configuration. However, elongate member 4302 may include any suitable configuration known in the art. In one embodiment, pusher 4300 may be sized to be advanced through tool 3000 to spacer 2700. At its proximal end 4304, pusher 4300 may include a handle 4305. Handle 4305 may include any suitable configuration. For example, handle 4305 may include a generally tubular structure. Handle 4305 may include a diameter that is relatively larger than a diameter of elongate member 4302. At its distal end 4306, elongate member may include a pushing member 4307. Pushing member 4307 may include any suitable configuration. For example, pushing member 4307 may be substantially tubular. In one embodiment, pushing member 4307 may include a diameter that is relatively larger than a diameter of elongate member 4302, but relatively smaller than a diameter of handle 4305.

Figure 44:
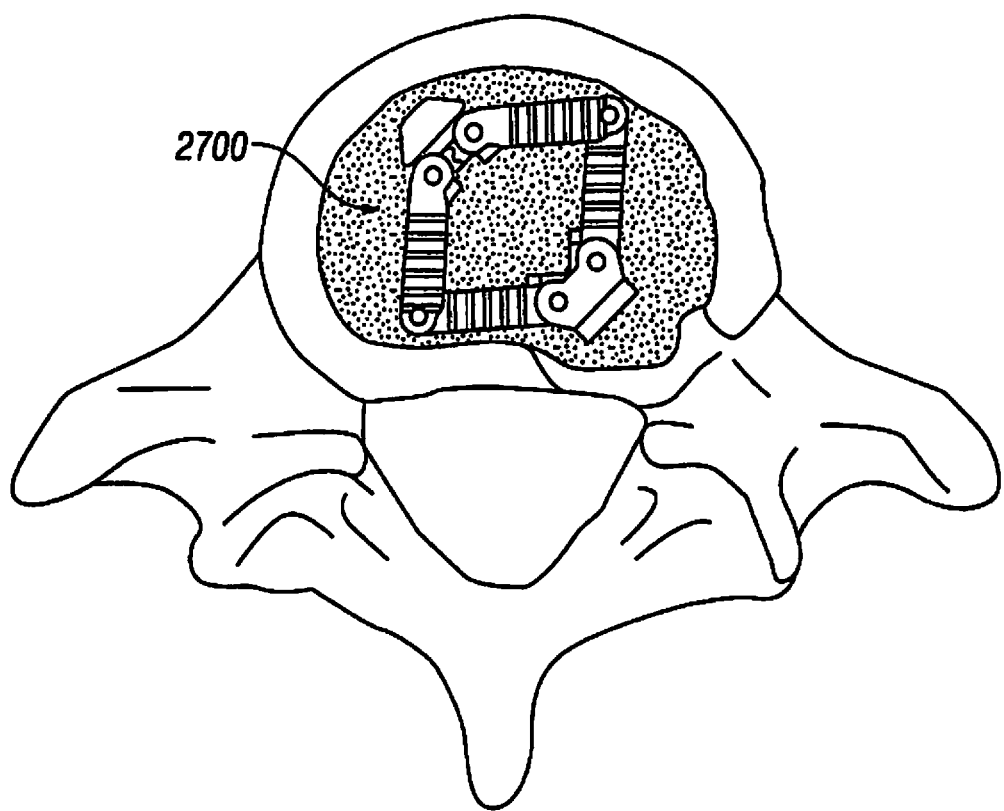
FIG. 44 depicts a final implanted configuration of an exemplary embodiment of an expandable interbody spacer.

In use, the bone funnel pusher 4300 may be used to fill spacer 2700 with, e.g., finely milled autogenous bone graft material to tightly pack spacer 2700. Once the graft material is tightly packed within spacer 2700, the inserter knob 3038 may be rotated to withdraw sleeve 3030 to disengage the inserter fork from spacer 2700. Prior to final disengagement, however, a user may choose to verify a final positioning of the spacer 2700 via radiographic visualization, such as, e.g., fluoroscopy, X-ray, or any other suitable imaging technique, as shown in FIG. 44.

If necessary, the spacer 2700 may be removed or otherwise manipulated by first inserting a removal tool (not shown) through a distal end of lumen 2744 in distal component 2740. The removal tool may engage locking feature 2760 and advance it completely back into cylindrical portion 2703 of proximal portion 2702, thereby removing the impediment to links 2710 and 2712 returning to their collapsed position. Next, projections 3024 of arms 3018, 3020 may engage features 2706 as described above. Threaded shaft 3200 may then be inserted through tool 3000 to engage threads 3208 within distal component 2740. Subsequently, hex cap 3700 may be provided over a proximal end of tool 3000 for rotation so as to collapse 2700 for removal from within the patient.

As described above, the devices, tools, and methods described herein may be used to provide an interbody spacer for positioning between adjacent vertebral bodies. Prior to performing the above-described steps, those of ordinary skill in the art will understand that a patient's native intervertebral disc may be first removed via a conventional discectomy, for example. Alternatively, scrapers may be used for disc distractions and to loosen the disc space without damaging vertebral endplates. In one embodiment, an operator may begin distraction with a relatively small scraper and proceed with increasingly larger scrapers. Next, the disc space may be prepared for receiving, for example, spacer 2700 as known in the art. Subsequently, measurements may be made of a height and width of the interbody disc space to ensure a spacer of correct dimensions is selected for implantation. The measurements may be made by any suitable means known in the art. For example, a user may conduct one or more adjustable footprint trials. In particular, one or more trials may be inserted into the prepared disc space in a collapsed configuration and expanded. The trial may be observed under suitable imaging means, such as, e.g., fluoroscopy, to identify appropriate sizing suitable for the prepared disc space.

While the invention herein disclosed has been described by means of specific embodiments and applications thereof, numerous modifications and variations can be made thereto by those skilled in the art without departing from the scope of the invention as set forth in the claims.

What is claimed is:

1. A system for treating a vertebral condition, the system comprising:
an interbody implant configured to transition between a first configuration and a second configuration, wherein the interbody implant comprises:
a first arm including a first end and a second end, wherein the first arm is defined by a plurality of links coupled to one another;
a second arm including a first end and a second end, wherein the second arm is defined by a plurality of links coupled to one another;
a proximal component coupled to the first ends of the first and second arms, wherein the proximal component includes a lumen with threads;
a distal component coupled to the second ends of the first and second arms; and
a locking feature received in the lumen, wherein the locking feature includes threads that engage the threads of the lumen; and
an instrument for positioning the implant within a patient, the instrument comprising:
a handle assembly comprising a holder element;
an elongate member received in the holder element, wherein the elongate member includes a fork-like end for grasping the interbody implant;
a sleeve positioned over the elongate member;
an actuator assembly operably attached to a proximal portion of the elongate member; and
a threaded shaft insertable into a proximal portion of the actuator assembly and through the sleeve,
wherein in the handle assembly has a longitudinal axis that is transverse to a longitudinal axis of the elongate member.

2. The system of claim 1, wherein the first configuration is a collapsed configuration and the second configuration is an expanded configuration.

3. The system of claim 1, wherein one or both of the proximal and distal components includes a passageway therethrough.

4. The system of claim 1, wherein the plurality of links defining the first arm are configured to engage each other to maintain a position of a first link of the plurality of links relative to another link of the plurality of links.

5. The system of claim 1, further comprising a locking mechanism for preventing the implant from returning to the second configuration from the first configuration when the locking mechanism is activated.

6. The system of claim 1, wherein a distal end of the elongate member includes a plurality of resilient arms.

7. The system of claim 6, wherein the sleeve is configured to urge at least one of the plurality of resilient arms towards the other of the plurality of resilient arms.

8. The system of claim 1, wherein a proximal end of the elongate member comprises one or more horizontal slits.

9. The system of claim 8, wherein the actuator assembly comprises one or more projections that are received in the one or more horizontal slits.

10. A method of positioning an interbody implant in a space between adjacent vertebral bodies, the method comprising:
positioning the interbody implant within the space using an instrument, wherein the interbody implant comprises:
a first arm including a first end and a second end, wherein the first arm is defined by a plurality of links rotatably coupled to one another;
a second arm including a first end and a second end, wherein the second arm is defined by a plurality of links rotatably coupled to one another;
a proximal component coupled to the first ends of the first and second arms, wherein the proximal component includes a lumen with threads; and
a distal component coupled to the second ends of the first and second arms;
transitioning the interbody implant from a first configuration to a second configuration; and
activating a locking mechanism to maintain the interbody implant in the second configuration,
wherein the instrument comprises:
a handle assembly comprising a holder element;
an elongate member received in the holder element, wherein the elongate member includes a fork-like end for grasping the interbody implant;
a sleeve positioned over the elongate member;
an actuator assembly operably attached to a proximal portion of the elongate member; and
a threaded shaft insertable into a proximal portion of the actuator assembly and through the sleeve,
wherein in the handle assembly has a longitudinal axis that is transverse to a longitudinal axis of the elongate member.

11. The method of claim 10, further comprising removing a native disc and preparing the space prior to inserting the expandable interbody implant.

12. The method of claim 10, further comprising measuring at least one of a height and a width dimension of the space.

13. The method of claim 10, wherein positioning the interbody implant within the space includes advancing the interbody implant to the space via a lateral approach.

14. The method of claim 10, wherein, in the second configuration, the interbody implant encloses a region defined by the first arm, the second arm, the proximal component, and the distal component.

15. The method of claim 10, further comprising delivering a material to the region.

16. The method of claim 10, wherein the plurality of links defining the first arm are configured to engage each other to maintain a position of a first link of the plurality of links relative to another link of the plurality of links.

17. The method of claim 10, further comprising visualizing the implant via fluoroscopy.

18. The method of claim 10, wherein the actuator assembly comprises one or more projections that are received in one or more horizontal slits of the elongate member.

* * * * *